United States Patent
Fujisawa et al.

(10) Patent No.: US 9,377,562 B2
(45) Date of Patent: Jun. 28, 2016

(54) MEDICAL DEVICE, AND METHOD FOR PRODUCING SAME

(75) Inventors: Kazuhiko Fujisawa, Otsu (JP); Rumiko Kitagawa, Otsu (JP); Masataka Nakamura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 77 days.

(21) Appl. No.: 14/239,074

(22) PCT Filed: Aug. 14, 2012

(86) PCT No.: PCT/JP2012/070704
§ 371 (c)(1),
(2), (4) Date: May 8, 2014

(87) PCT Pub. No.: WO2013/024856
PCT Pub. Date: Feb. 21, 2013

(65) Prior Publication Data
US 2014/0240660 A1 Aug. 28, 2014

(30) Foreign Application Priority Data
Aug. 17, 2011 (JP) ................. 2011-178664

(51) Int. Cl.
*G02C 7/00* (2006.01)
*A61L 33/00* (2006.01)
*A61K 6/08* (2006.01)
*G02B 1/04* (2006.01)
*A61L 27/18* (2006.01)
*A61L 27/34* (2006.01)
*A61L 27/50* (2006.01)
*A61L 27/52* (2006.01)
*B29D 11/00* (2006.01)
*G02C 7/04* (2006.01)
*G02B 1/18* (2015.01)

(52) U.S. Cl.
CPC ............... *G02B 1/043* (2013.01); *A61L 27/18* (2013.01); *A61L 27/34* (2013.01); *A61L 27/50* (2013.01); *A61L 27/52* (2013.01); *B29D 11/00038* (2013.01); *B29D 11/00865* (2013.01); *G02B 1/18* (2015.01); *G02C 7/04* (2013.01); *A61L 2400/10* (2013.01); *A61L 2420/06* (2013.01); *A61L 2430/16* (2013.01)

(58) Field of Classification Search
CPC ........ G02B 1/043; A61L 27/34; A61L 27/52; B29D 11/00865
USPC ........ 523/105, 107, 203; 351/159.33; 427/2.1
See application file for complete search history.

(56) References Cited

U.S. PATENT DOCUMENTS

| | | | |
|---|---|---|---|
| 4,153,641 A | 5/1979 | Deichert et al. | |
| 4,277,595 A | 7/1981 | Deichert et al. | |
| 4,543,398 A | 9/1985 | Bany et al. | |
| 4,954,586 A | 9/1990 | Toyoshima et al. | |
| 5,804,318 A * | 9/1998 | Pinchuk et al. | 428/421 |
| 5,994,488 A | 11/1999 | Yokota et al. | |
| 6,361,768 B1 * | 3/2002 | Galleguillos et al. | 424/70.12 |
| 6,451,871 B1 | 9/2002 | Winterton | |
| 6,634,748 B1 | 10/2003 | Vanderlaan et al. | |
| 2001/0045676 A1 | 11/2001 | Winterton et al. | |
| 2002/0006521 A1 | 1/2002 | Shimoyama et al. | |
| 2003/0235604 A1 * | 12/2003 | McGee et al. | 424/429 |
| 2004/0047979 A1 | 3/2004 | Qiu et al. | |
| 2004/0077232 A1 * | 4/2004 | Ebner et al. | 439/894 |
| 2008/0097575 A1 * | 4/2008 | Cottone | 623/1.13 |
| 2008/0174035 A1 | 7/2008 | Winterton | |

FOREIGN PATENT DOCUMENTS

| | | |
|---|---|---|
| JP | 54-24047 | 2/1979 |
| JP | 54-081363 | 6/1979 |
| JP | 56-51715 | 5/1981 |
| JP | 59-229524 | 12/1984 |
| JP | 2-188717 | 7/1990 |
| JP | 2-503890 | 11/1990 |
| JP | 3-240021 | 10/1991 |
| JP | 03-257420 | 11/1991 |
| JP | 05-5861 | 1/1993 |
| JP | 6-508645 | 9/1994 |
| JP | 10-201840 | 8/1998 |
| JP | 10-212355 | 8/1998 |
| JP | 2002-501211 | 1/2002 |
| JP | 2002-047365 | 2/2002 |
| JP | 2003529416 | 10/2003 |
| JP | 2004-517163 | 6/2004 |
| JP | 2002-501211 | 10/2005 |
| JP | 2005-538418 | 12/2005 |
| JP | 2007-526364 | 9/2007 |
| JP | 2009-540369 | 11/2009 |
| WO | WO 89/07520 | 8/1989 |

(Continued)

OTHER PUBLICATIONS

International Search Report corresponding to PCT/JP2012/070704 dated Sep. 18, 2012.
Extended European Search Report for European Application No. 12823447.3-1553 mailed Mar. 17, 2015.
Japanese Final Rejection Office Action With English Translation Based On Corresponding Japanese Patent Application No. 2012-548276, Issued May 9, 2016.

*Primary Examiner* — Tae H Yoon
(74) *Attorney, Agent, or Firm* — Ratnerprestia

(57) ABSTRACT

A medical device includes a layer made of an acidic polymer and a basic polymer formed on at least a part of a surface of a base material, wherein at least one kind of an acidic polymer and a basic polymer forming the layers made of the acidic polymer and the basic polymer is a multi-component copolymer of three or more components.

15 Claims, 2 Drawing Sheets

(56) References Cited

FOREIGN PATENT DOCUMENTS

| WO | WO 93/00391 | 1/1993 |
| WO | WO 99/35520 | 7/1999 |
| WO | WO 01/57118 A2 | 8/2001 |
| WO | WO 2005/078482 | 8/2005 |
| WO | 2008095955 | 8/2008 |
| WO | WO 2008/127299 A2 | 10/2008 |

* cited by examiner

MEDICAL DEVICE, AND METHOD FOR PRODUCING SAME

CROSS REFERENCE TO RELATED APPLICATIONS

This application is the U.S. National Phase Application of the PCT International Application No. PCT/JP2012/070704, filed Aug. 14, 2012, which claims priority to Japan Patent Application No. 2011-178664, filed Aug. 17, 2011, the contents of each of these applications being incorporated by reference herein in their entireties for all purposes.

FIELD OF THE INVENTION

The present invention relates to a medical device and a method for producing the same

BACKGROUND OF THE INVENTION

As one of medical devices, a soft contact lens (a soft ophthalmic lens) is exemplified. In a commercially available soft contact lens, a hydrogel material having a water content of about 25% to about 80% is usually used. A water-containing soft contact lens made of a hydrogel material, however, causes a phenomenon that water evaporates from the contact lens because the contact lens contains water. By this phenomenon, certain percentage of contact lens wearers may feel dryness stronger than when the wearers are naked eye and may feel uncomfortable. Some wearers who complain of symptoms called contact lens dry eye have existed. In addition, a water-containing soft contact lens made of a hydrogel material is easily contaminated with components in a lacrimal fluid and contains large amount of water, and therefore, the lens also has a risk of bacterial proliferation. Moreover, although a silicone hydrogel material, which is a hydrogel material further containing a silicone component, has high oxygen permeability, and lipid stains easily adhere to the surface because the silicone component is hydrophobic. A problem that the lipid stain adhesion is not completely improved therefore arises even if a hydrophilic polymer such as polyacrylic acid is coated.

On the other hand, as a low water content soft contact lenses having high oxygen permeability, for example, a silicone rubber lens obtained by a method in which a platinum catalyst is added to a mixture of a polydimethylsiloxane in which both molecular ends are blocked with vinylmethylsilyl groups and a methyl hydrogen polysiloxane and the mixture is heated and cured by the molding method is known (Patent Literature 1).

In addition, contact lens materials having high oxygen permeability mainly made of polysiloxane having a plurality of polymerizable functional groups are also described in Patent Literatures 2 to 6. Among these Patent Literatures, in Patent Literature 6, a contact lens material made of a polymer obtained by polymerizing only bifunctional organic siloxane macromers or copolymerizing the macromers with other monomers is disclosed. As the monomer used for the copolymerization, an acrylic acid fluoroalkyl ester or a methacrylic acid fluoroalkyl ester and an acrylic acid alkyl ester or a methacrylic acid alkyl ester are disclosed.

However, in a conventional low water content soft contact lenses having high oxygen permeability, the following problems are also observed. The silicone rubber lens described in Patent Literature 1 has disadvantages that a hydrophilic treatment layer that is provided for improving a hydrophobic property of a lens surface is peeled and that fixation to a cornea occurs because of too large elasticity, and thus, has not been widely used in practical use.

The materials mainly made of a polysiloxane having a plurality of polymerizable functional groups described in Patent Literatures 2 to 6 have high oxygen permeability as well as flexibility, and therefore, the materials are considered as one of the materials suitable for a contact lens. However, the materials may cause fixation to a cornea because tackiness remains on the lens surface after polymerization and the lens has insufficient balance between flexibility and mechanical properties such as folding resistance.

Various methods have been known with respect to a method for modifying a surface of a medical device. Among them, methods of coating two or more polymer materials layer by layer and stacking the layers have been known (Patent Literatures 7 to 9). Among these methods, a method of alternately coating polymer materials having two opposite charges layer by layer is called an LbL method. The layers of each material are considered to be bonded to other layers made of a different material in a noncovalent bonding manner. However, high oxygen permeability soft ophthalmic lenses in which usefulness of this method is clearly described are only lenses made of a silicone hydrogel material and usefulness to a low water content soft ophthalmic lens has not been known. In addition, a conventional LbL coating has been carried out for many layers such as about 4 layers to about 20 layers, and therefore, a production process may become longer and a production cost may be increased.

PATENT LITERATURE

Patent Literature 1: Japanese Patent Application Laid-open No. 54-81363
Patent Literature 2: Japanese Patent Application Laid-open No. 54-24047
Patent Literature 3: Japanese Patent Application Laid-open No. 56-51715
Patent Literature 4: Japanese Patent Application Laid-open No. 59-229524
Patent Literature 5: Japanese Patent Application Laid-open No. 2-188717
Patent Literature 6: Japanese Patent Application Laid-open No. 5-5861
Patent Literature 7: Japanese National Publication of International Patent Application No. 2002-501211
Patent Literature 8: Japanese National Publication of International Patent Application No. 2005-538418
Patent Literature 9: Japanese National Publication of International Patent Application No. 2009-540369

SUMMARY OF THE INVENTION

The present invention is aimed at solving the problems described above. With respect to a low water content base material, the present invention aims to provide a medical device that significantly reduces or avoids a phenomenon that a contact lens adheres to a cornea and the like at the time of wearing the contact lens by improving wettability and a lubricity, and reduces a risk of bacterial proliferation by improving an antifouling property to body fluids such as a lacrimal fluid. In addition, with respect to a water-containing base material, the present invention aims to provide a medical device having adequate wettability and lubricity and having excellent lipid adhesion resistance. The present invention also aims to produce the medical device inexpensively by a simple process.

The present invention includes the following constitution.

A medical device according to an embodiment of the present invention includes a layer made of an acidic polymer and a basic polymer formed on at least a part of a surface of a base material, wherein at least one kind of an acidic polymer and a basic polymer forming the layer made of the acidic polymer and the basic polymer is a multi-component copolymer of three or more components.

In the above, it is preferable that the layer made of the acidic polymer and the basic polymer is formed by carrying out treatment with one or more kinds of an acidic polymer solution one or more times and carrying out treatment with one or more kinds of a basic polymer solution one or more times.

Moreover, in the above, it is preferable for the present invention that the multi-component copolymer of three or more components comprises one or more kinds of each of an acidic monomer or a basic monomer, a monomer having a hydroxy group, and a monomer having an amide group.

One preferable aspect of the present invention provides a method for producing a medical device including the following step 1 to step 4 in this order:
<Step 1>
polymerizing a mixture including a monomer having a siloxanyl group to obtain a molding;
<Step 2>
contacting the molding to an acidic polymer solution, and thereafter, washing and removing the excessive acidic polymer solution;
<Step 3>
contacting the molding to a basic polymer solution, and thereafter, washing and removing the excessive basic polymer solution; and
<Step 4>
contacting the molding to an acidic polymer solution of a multi-component copolymer containing three or more components, and thereafter, washing and removing the excessive acidic polymer solution.

The medical device of the present invention has excellent lubricity and wettability, and therefore, the phenomenon that an ophthalmic lens adheres to a cornea at the time of wearing the ophthalmic lens, which is considered as a problem of a conventional low water content soft ophthalmic lens, can be significantly reduced or avoided. In addition, in the medical device of an embodiment of the present invention, a layer made of an acidic polymer and a basic polymer is provided by treating the medical device with a solution of at least a kind of multi-component copolymer of three or more components, and therefore, the risk of bacterial proliferation can be reduced by improving an antifouling property to a body liquid such as a lacrimal fluid. In addition, according to a preferable aspect of the present invention, a medical device having high oxygen permeability, excellent wettability, excellent wearing feeling by being flexible, and excellent mechanical properties such as folding resistance can be provided. The medical device of the present invention also has an advantage that the medical device can be produced inexpensively in a simple process.

DETAILED DESCRIPTION OF EMBODIMENTS OF THE INVENTION

Figure 1:
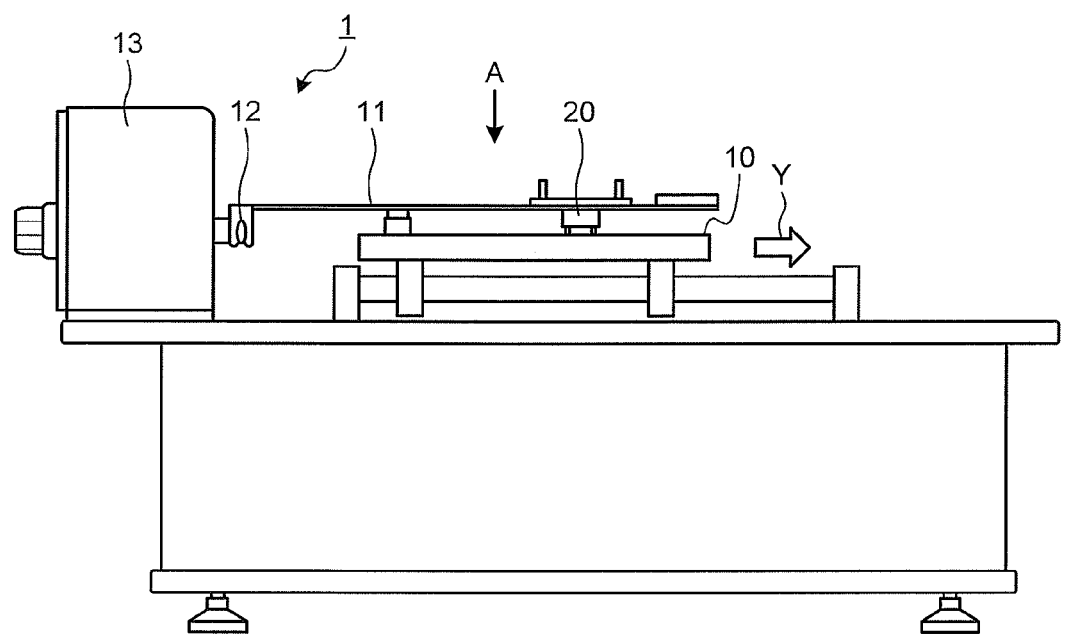
FIG. 1 is a schematic diagram illustrating an apparatus for measuring a surface friction coefficient of samples of a medical device according to an embodiment of the present invention.

A medical device used in the present invention means a device that is used for medical use and is used by being in contact with a patient or being in contact with a tissue taken from a patient such as blood or other body fluids. Preferably, ophthalmic lenses, endoscopes, catheters, infusion tubes, gas transport tubes, stents, sheaths, cuffs, tube connectors, access ports, drainage bags, blood circuits, skin materials, or drug carriers can be exemplified.

In the base material used in the medical device of the present invention, a low water content base material means a base material having a water content of 10% by mass or less, and a water-containing base material means a base material having a water content of more than 10% by mass.

Here, the water content is determined by, for example, {(Mass in wet state)−(Mass in dry state)/Mass in wet state} from a mass in a dry state of a test specimen having a film shape and a mass after wiping off the surface water of the test specimen in a wet state by a borate buffer solution.

In the case of the low water content base material, particularly in the case of use as an ophthalmic lens, the water content of the medical device of the present invention is preferably 10% by mass or less, more preferably 5% by mass or less, and further preferably less than 1% by mass.

In the case of the water-containing base material, particularly in the case of use as an ophthalmic lens, the water content of the medical device of the present invention is preferably 12 to 80% by mass, more preferably 20 to 60% by mass, and further preferably 30 to 50% by mass.

In a copolymer used for the layer made of an acidic polymer and a basic polymer of the medical device of the present invention, a copolymer of "n components" represents a copolymer obtained by copolymerizing n kinds of monomers. Here, as a mass of a copolymer is determined to be a standard (100% by mass), a monomer having a content of less than 0.1% by mass in the case of the acidic monomer and the basic monomer and less than 1% by mass in the case of another monomer are not counted as a kind of monomer. In addition, a multi-component copolymer means a copolymer of three or more components, that is, a copolymer obtained by copolymerizing three or more kinds of monomers.

A multi-component copolymer used in the medical device of the present invention is a copolymer made of preferably 10 components or less, more preferably 7 components or less, further preferably 5 components or less, and most preferably 3 components because, when kinds of copolymerization monomers are too many, a copolymerization ratios of each monomer are relatively too low, and therefore, expected physical properties cannot be provided. The multi-component copolymer may be a random copolymer or a block copolymer, and may be a copolymer in which only a part of the components is a block copolymer and the other components are a random copolymer.

A tensile modulus of the medical device of the present invention is preferably 0.01 to 5 MPa, more preferably 0.1 to 3 MPa, further preferably 0.1 to 2 MPa, particularly preferably 0.1 to 1 MPa, and most preferably 0.1 to 0.6 MPa. When the tensile modulus is too small, the medical device tends to be difficult to handle because the medical device is too soft. When the tensile modulus is too large, the medical device tends to have bad wearing feeling because the medical device is too stiff. When the tensile modulus is 2 MPa or less, excellent wearing feeling is obtained and when 1 MPa or less, more excellent wearing feeling is obtained, which is preferable. The tensile modulus is measured using a sample in a wet state.

A tensile elongation (elongation at break) of the medical device of the present invention is preferably 100% to 1000% and more preferably 200% to 700%. When the tensile elongation is small, the medical device becomes easy to break, which is not preferable. When the tensile elongation is too large, the medical device tends to be easy to deform, which is not preferable. The tensile elongation is measured using a sample in a wet state.

It is important from the viewpoint of bioaffinity that the surface of the medical device of the present invention has excellent wettability, and therefore, a dynamic contact angle (at the time of advance, immersion rate: 0.1 mm/sec) is preferably 100° or less, more preferably 90° or less, and further preferably 80° or less. From the viewpoint of preventing the medical device from sticking to a cornea of a wearer, the dynamic contact angle is preferably lower, and is preferably 65° or less, more preferably 60° or less, further preferably 55° or less, particularly preferably 50° or less, and most preferably 45° or less. The dynamic contact angle is measured to a borate buffer solution using a sample in a wet state by the borate buffer solution.

It is also important from the viewpoint of bioaffinity that the surface of the medical device of the present invention has excellent wettability and the wettability is particularly important from the viewpoint of preventing from sticking to a cornea of a wearer when the medical device is used as an ophthalmic lens. From this viewpoint, liquid film retention time of the surface of the medical device is preferably longer. Here, the liquid film retention time is a time in which a liquid film on the surface of the medical device is not broken but retained when the medical device immersed into a borate buffer solution is pulled out from the solution and retained so that the surface (a diameter direction in the case of an ophthalmic lens) is set to a vertical state in the air. The liquid film retention time is preferably 5 seconds or more, further preferably 10 seconds or more, and most preferably 20 seconds or more. Here, the diameter is a diameter of a circle constituted by an edge part of the lens. The liquid film retention time is measured using a sample in a wet state by the borate buffer solution.

Figure 2:
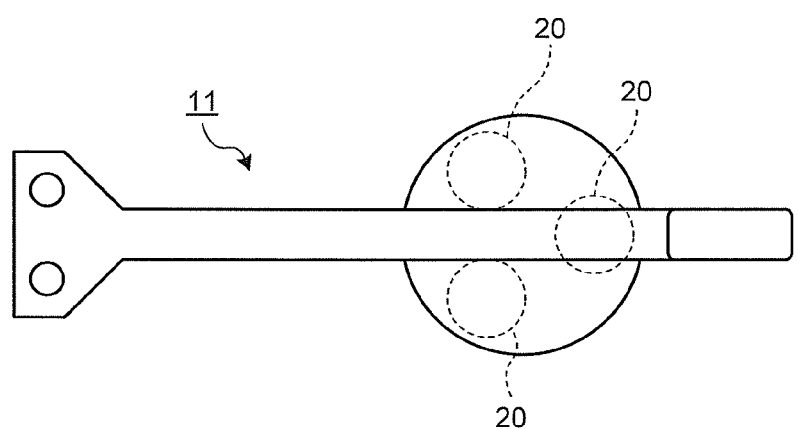
FIG. 2 is a schematic diagram illustrating constitution of a main part of a measuring jig and a friction element in the surface friction coefficient measurement apparatus illustrated in FIG. 1.
Figure 3:
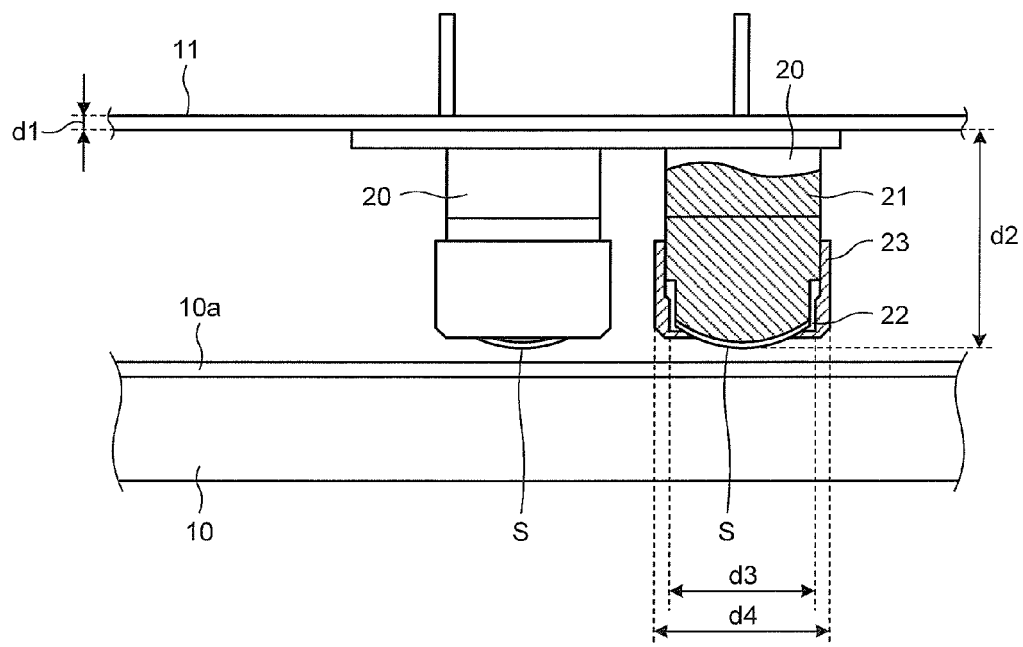
FIG. 3 is a partial sectional view illustrating constitution of the main part of the measuring jig and the friction element in the surface friction coefficient measurement apparatus illustrated in FIG. 1.

From the viewpoint of facilitating the movement when the medical device is in contact with a surface of a body tissue, and particularly from the viewpoint of preventing sticking to a cornea of a wearer in the case of an ophthalmic lens, the surface of the medical device preferably has excellent lubricity. As in Examples in this specification, lubricity can be evaluated by sensory evaluation when the medical device is rubbed five times with human fingers. The evaluation of the lubricity of the medical device of the present invention is preferably C or higher, more preferably B or higher, and most preferably A or higher. As an indicator for indicating the lubricity more objectively and quantitatively, it is also possible to evaluate by using a surface friction coefficient ratio as measured by the following method. The surface friction coefficient is measured by using a contact lens-shaped sample or a film-shaped sample that is cut out in a circular shape with a diameter of 14 mm. Friction Tester KES-SE (Kato Tech Co., Ltd.) is used to measure the surface friction coefficient. FIG. 1 is a schematic diagram illustrating an apparatus for measuring the surface friction coefficient of samples of the medical device according to the present invention. FIG. 2 is a schematic diagram illustrating the constitution of a main part of a measuring jig and a friction element for measuring the surface friction coefficient of the sample of the medical device according to the present invention seen from a direction of an arrow A illustrated in FIG. 1. FIG. 3 is a partial sectional view illustrating the constitution of the main part of the measuring jig and the friction element for measuring the surface friction coefficient of the sample of the medical device according to the present invention. First, a plate of "Teflon (registered trademark)" (manufactured by DuPont) (65 mm×100 mm×1.0 mm, not illustrated in FIG. 3) is horizontally placed on a sample stage 10 of an apparatus 1, and then a quartz glass plate 10a (55 mm×90 mm×1.0 mm) having a smooth surface is horizontally placed on the sample stage 10 and fixed. The plate of "Teflon (registered trademark)" (manufactured by DuPont) and the quartz glass plate having sufficiently high flatness are used. Here, the quartz glass plate 10a has a state in which the surface is wiped off with Kimwipe (registered trademark)" (manufactured by Nippon Paper Crecia Ltd.) to be clean and dry for each measurement. In the measurement, the measurement is carried out by attaching three pieces of samples S to a friction element 20 of a measurement jig 11 (a weight of 62 g=W) illustrated in FIGS. 2 and 3. At this time, the sample S are placed on an apex of a mounting holder 21 of the friction element 20, and thereafter the sample S are held by a gasket 22 and fixed by a nut 23. In a state that the samples S are projected from the apex of the 20 friction element and fixed, each of 0.1 mL of the borate buffer solution in the case of the following condition A or physiologic saline in the case of the following condition B is dropped at each central portion of the three samples. Thereafter, the measurement jig 11 is rapidly attached to the apparatus 1. In a state that all three samples S are in contact with the quartz glass plate 10a, a stress (F) in a horizontal direction when the sample stage 10 is moved in a horizontal direction (an arrow Y) at a speed of 1.0 mm/second is detected by a friction detection part 12 and measured by a force measuring device 13.

The surface friction coefficient (MIU) is determined form the following formula.

$$MIU=F/W$$

A moving distance is set to 30 mm, and the measurement of MIU is carried out in every 0.1 seconds.

The surface friction coefficient is determined to be an average value of MIU in an interval (at least 5 mm) where MIU in a travel distance of 5 mm to 25 mm is stabilized (a value obtained by dividing the sum of MIU at each time in the interval with the number of data of MIU).

At this time, a surface friction coefficient in the condition A is defended as $MIU_a$ and a surface friction coefficient in the condition B is defended as $MIU_b$.

Condition A: To carry out measurements using samples in the wet state by the borate buffer solution.

Condition B: To carry out measurements using samples in the wet state by the physiologic saline.

In FIG. 3, the thickness of a support plate for supporting the friction element 20 the measurement jig 11 is defined as d1. In the friction element 20, when a projection length from the measurement jig 11 is defined as d2, a diameter of a portion in contact with the lens in the mounting holder 21 being defined as d3, and a diameter of the outer periphery of the nut 23 being defined as d4, d1 is 1.5 (mm); d2 is 22.4 (mm); d3 is 14 (mm), and d4 is 18 (mm).

A surface friction coefficient in the condition A ($MIU_o$) of "Acuvue (registered trademark) Oasys" (Johnson & Johnson, Inc.) in the method described above is determined. Surface friction coefficient ratios $Q_a$ and $Q_b$ are determined by the following formula.

$$Q_a = MIU_a/MIU_o$$

$$Q_b = MIU_b/MIU_o$$

A smaller surface friction coefficient ratio ($Q_b$ and $Q_a$) described later that is measured by the method described above is preferable.

Furthermore, in the friction described above, the surface friction coefficient ratio ($Q_a$) of the medical device of the present invention at the time of wetting with the borate buffer solution is preferably 2 or less, more preferably 1.6 or lower, and further preferably 1 or less. It should be noted that:

$$Q_a = MIU_a/MIU_o$$

where $MIU_a$ represents the surface friction coefficient between the medical device and the smooth quartz glass plate in the wet state by the borate buffer solution. $MIU_o$ represents a surface friction coefficient between "Acuvue (registered trademark) Oasys" and the smooth quartz glass plate in the wet state by the borate buffer solution.

The smaller the surface friction coefficient ratio $Q_a$, the smaller the surface friction and the smaller the influence on a living body when rubbing is caused between the medical device and the living body (for example, cornea or palpebral conjunctiva in the case of a contact lens), which is preferable. In this sense, the surface friction coefficient ratio $Q_a$ is preferably 1 or less, more preferably 0.8 or less, and most preferably 0.6 or less.

In addition, the surface friction coefficient ratio $Q_b$ at the time of wetting by the physiologic saline is preferably 3 or less, more preferably 2 or less, and further preferably 1.5 or less. It should be noted that:

$$Q_b = MIU_b/MIU_o$$

where $MIU_b$ represents the surface friction coefficient between the medical device and the smooth quartz glass plate in the wet state by the physiologic saline.

In the medical device in which a layer made by an acidic polymer and a basic polymer is formed on at least a part of a base material, which is one of the preferable aspects of the present invention, it has been found that $Q_b$ tends to be larger than $Q_a$ and $Q_b$ is significantly large in some cases. The physiologic saline, however, is a similar liquid to body fluids (for example, lacrimal fluid in the case of a contact lens), and, from the viewpoint of preventing sticking of the medical device to a surface of a living body (a cornea in the case of an ophthalmic lens), it is preferable that the surface friction coefficient ratio ($Q_b$) at the time of wetting by the physiologic saline is also small.

The smaller the surface friction coefficient ratio $Q_b$, the smaller the surface friction and the smaller the influence on a living body when rubbing is caused between the medical device and the living body (for example, cornea or palpebral conjunctiva in the case of a contact lens), which is preferable. In this sense, the surface friction coefficient ratio $Q_b$ is preferably 1.5 or less, more preferably 1.0 or less, and most preferably 0.8 or less.

Furthermore, in the medical device of the present invention, difference between the surface friction coefficient ratio $Q_b$ at the time of wetting by the borate buffer solution and the surface friction coefficient ratio $Q_a$ at the time of wetting by the physiologic saline ($Q_b - Q_a$) is preferably 1.6 or less, more preferably 1.3 or less, and further preferably 1.0 or less. When the difference between the surface friction coefficient ratio $Q_a$ and the surface friction coefficient ratio $Q_b$ is small, difference between lubricity at the time of applying the medical device to a living body to lubricity at the time before application (for example, at the time of opening package) tends to be small, which is preferable.

Antifouling properties of the medical device of the present invention can be evaluated by mucin adhesion, lipid (methyl palmitate) adhesion, and an immersion test into artificial lacrimal fluid. The smaller the adhesion amount measured by these evaluations, the more excellent the wearing feeling and the less the risk of bacterial proliferation, which is preferable. An adhesion amount of mucin when a low water content base material is used is preferably 5 $\mu g/cm^2$ or less, more preferably 4 $\mu g/cm^2$ or less, and most preferably 3 $\mu g/cm^2$ or less.

From the viewpoint of oxygen supply from the atmosphere to a body tissue of a patient (an eye in the case of ophthalmic lens), the medical device of the present invention preferably has high oxygen permeability. An oxygen permeability coefficient [$\times 10^{-11}$ ($cm^2$/sec)·$mLO_2$/(mL·hPa)] is preferably 30 to 2000, more preferably 45 to 1500, further preferably 65 to 1000, and most preferably 75 to 700. When the oxygen permeability coefficient is set to too large, other properties such as mechanical properties may be adversely affected, which is not preferable. The oxygen permeability is measured using a sample in a dry state.

Depending on used application, the medical device of an embodiment of the present invention includes formed bodies having a lens shape or a sheet-like shape (hereinafter, referred to as a base material), and a layer made of an acidic polymer and a basic polymer is formed on at least a part of the surface of the base material.

In order to have high oxygen permeability and in order to obtain strong adhesion not though covalent bonds between the base material and a polymer coated to the surface, the base material preferably contains 5% by mass or more of silicon atoms. A content of the silicon atoms (% by mass) is calculated based on a mass of the base material in a dry state as a standard (100% by mass). A content of the silicon atoms in the base material is preferably 5% by mass to 36% by mass, more preferably 7% by mass to 30% by mass, further preferably 10% by mass to 30% by mass, and most preferably 12% by mass to 26% by mass. When the content of the silicon atoms is too large, the tensile modulus may be high, which is not preferable.

A content of the silicon atoms in the base material can be measured by the following method. A sufficiently dried base material is weighed and charged into a platinum crucible, and sulfuric acid is added and the mixture is heated with a hot plate and a burner to form ash. The ash is melted with sodium carbonate and water is added to the mixture to dissolve with heat. Thereafter, nitric acid is added and a solution having a constant volume is made with water. For this solution, silicon atoms are measured by ICP emission spectroscopy, and a content in the base material is determined.

When the medical device of the present invention is used as an ophthalmic lens, high transparency is preferable because the ophthalmic lens is an optical product. As a criterion of the transparency, it is preferable that the lens is clear and has no turbidity when the lens is visually observed. Moreover, when an ophthalmic lens is observed with a lens projector, it is preferable that turbidity is hardly observed or is not observed at all and it is the most preferable that turbidity is not observed at all.

When an application of the medical device is an ophthalmic lens, a total light transmittance of the medical device of the present invention is preferably 85% or more, more preferably 88% or more, and most preferably 91% or more in a wet state of the ophthalmic lens in terms of quality.

As one aspect, preferably, a base material of the medical device according to the present invention includes a polymer of a component A that has a plurality of polymerizable functional groups per molecule and is a polysiloxane compound having a number average molecular weight of 6000 or more or a copolymer of the component A and other compound having a polymerizable functional group other than the component A as a main component. Here, the main component means a component that is included in 50% by mass or more when a mass of the base material in a dry state is determined to be a standard (100% by mass).

In this specification, a polysiloxane compound is a compound having a Si—O—Si—O—Si bond. The Si—O—Si—O—Si bond is made of continuous Si—O—Si bonds (a siloxanyl group).

A number average molecular weight of the component A is preferably 6000 or more. The inventors of the present invention have found that, when the number average molecular weight of the component A is in this range, the medical device having flexibility, excellent wearing feeling, and excellent mechanical properties such as folding resistance can be obtained. The number average molecular weight of the polysiloxane compound of the component A is preferably 8000 or more because the base material having excellent mechanical properties such as folding resistance can be obtained. The number average molecular weight of the component A is preferably in a range of 8000 to 100000, more preferably in a range of 9000 to 70000, and further preferably in a range of 10000 to 50000. When the number average molecular weight of the component A is too small, mechanical properties such as folding resistance tends to deteriorate, and particularly when the number average molecular weight is less than 6000, the folding resistance deteriorates. When the number average molecular weight of the component A is too large, flexibility and transparency tend to deteriorate, which is not preferable.

A dispersity of the component A (a value calculated by dividing a mass average molecular weight by a number average molecular weight) is preferably 6 or less, more preferably 3 or less, further preferably 2 or less, and most preferably 1.5 or less. When the dispersity of the component A is small, advantages that transparency of the obtained medical device is improved because compatibility with other components is improved; extractable components included in the obtained medical device is reduced; and a shrinkage ratio associated with medical device molding is reduced are generated. When the medical device is used as an ophthalmic lens, the shrinkage ratio associated with lens molding is evaluated by a lens molding ratio=[Lens diameter]/[Diameter of mold cavity]. As the lens molding ratio is closer to 1, it is easier to produce a high quality lens stably. The molding ratio is preferably in a range of 0.85 to 2.0, more preferably in a range of 0.9 to 1.5, and most preferably in a range of 0.91 to 1.3.

In the present invention, the number average molecular weight of the component A is an number average molecular weight in terms of polystyrene measured by a gel permeation chromatography method (a GPC method) using chloroform as a solvent. The mass average molecular weight and the dispersity (the value calculated by dividing a mass average molecular weight by a number average molecular weight) are measured in a similar method.

Here, in this specification, the mass average molecular weight may be represented by Mw and the number average molecular weight may be represented by Mn. In addition, a molecular weight of 1000 may be represented as 1 kD. For example, a "Mw of 33 kD" represents a "mass average molecular weight of 33000".

The component A is a polysiloxane compound having a plurality of polymerizable functional groups. The number of the polymerizable functional group of the component A may be two or more per molecule, and, from the viewpoint that a more flexible (low modulus) base material is easily obtained, the number is preferably two per molecule. The component A may have the polymerizable functional groups in any position in a molecular chain, and preferably has a structure in which both ends of the molecular chain have polymerizable functional groups.

The polymerizable functional group of the component A is preferably a radical polymerizable functional group and more preferably a functional group having a carbon-carbon double bond. Examples of the preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residues, an isocrotonic acid residue, and a citraconic acid residue. Among them, the (meth)acryloyl group is the most preferable functional group because the (meth)acryloyl group is highly polymerizable. When the component A has two or more polymerizable functional group in a molecule, polymerizable functional groups in a molecule may be the same as or different from each other.

Here, in this specification, the term "(meth)acryloyl" represents both of methacryloyl and acryloyl, and the terms "(meth)acrylic acid" and "(meth)acrylate" have similar meaning.

As the component A, a component having the following formula (A1) is preferable.

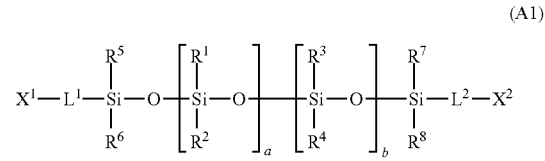

(A1)

In formula (A1), $X^1$ and $X^2$ each independently represents a polymerizable functional group. $R^1$ to $R^8$ each independently represents a substituent selected from hydrogen, an alkyl group having a carbon number of 1 to 20, a phenyl group, and a fluoroalkyl group having a carbon number of 1 to 20. $L^1$ and $L^2$ each independently represents a divalent group. a and b each independently represents an integer of 0 to 1500. Here, a and b are not zero at the same time.

$X^1$ and $X^2$ are preferably radical polymerizable functional groups and more preferably functional groups having a carbon-carbon double bond. Examples of the preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residues, an isocrotonic acid residue, and a citraconic acid residue. Among them, the (meth)acryloyl group is the most preferable functional group because the (meth)acryloyl group is highly polymerizable.

Specific preferable examples of $R^1$ to $R^8$ include hydrogen; an alkyl group having a carbon number of 1 to 20 such as a methyl group, an ethyl group, a propyl group, an isopropyl group, a butyl group, a t-butyl group, a decyl group, a dodecyl group, and an octadecyl group; a phenyl group, and a fluoroalkyl group having a carbon number of 1 to 20 such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a pentafluoropropyl group, a tetradecafluorooctyl group, a pentadecafluorooctyl group, an octadecafluorodecyl group, and a nonadecafluorodecyl group. Among them, from the viewpoint of providing excellent mechanical properties and high oxygen permeability to the medical device, more preferable is hydrogen and a methyl group, and the most preferable is a methyl group.

As $L^1$ and $L^2$, a divalent group having a carbon number of 1 to 20 is preferable. Among them, groups represented by the following formulae (LE1) to (LE12) are preferable; among them, the groups represented by the following formulae (LE1), (LE3), (LE9), and (LE11) are more preferable; the groups represented by the following formulae (LE1) and (LE3) are further preferable; and the group represented by the following formula (LE1) is the most preferable, because these groups have an advantage that the compound of formula (A1) is easily obtained in high purity. Here, the following formulae (LE1) to (LE12) are illustrated as an end bonding to the polymerizable functional group $X^1$ or $X^2$ is in the left side and an end bonding to silicon atom is in the right side.

$OCH_2CH_2CH_2$ (LE1)

$NHCH_2CH_2CH_2$ (LE2)

$OCH_2CH_2NHCOOCH_2CH_2CH_2$ (LE3)

$OCH_2CH_2NHCONHCH_2CH_2CH_2$ (LE4)

$OCH_2CH_2CH_2CH_2$ (LE5)

$NHCH_2CH_2CH_2CH_2$ (LE6)

$OCH_2CH_2NHCOOCH_2CH_2CH_2CH_2$ (LE7)

$OCH_2CH_2NHCONHCH_2CH_2CH_2CH_2$ (LE8)

$OCH_2CH_2OCH_2CH_2CH_2$ (LE9)

$NHCH_2CH_2OCH_2CH_2CH_2$ (LE10)

$OCH_2CH_2NHCOOCH_2CH_2OCH_2CH_2CH_2$ (LE11)

$OCH_2CH_2NHCONHCH_2CH_2OCH_2CH_2CH_2$ (LE12)

In addition, in formula (A1), a and b each independently represents an integer of 0 to 1500. Here, a and b are not zero at the same time. (a+b), which is a total value of a and b, is preferably 80 or more, more preferably 100 or more, more preferably 100 to 1400, more preferably 120 to 950, and further preferably 130 to 700.

In formula (A1), when all of $R^1$ to $R^8$ are methyl groups, b equals to 0, and a is preferably 80 to 1500, more preferably 100 to 1400, more preferably 120 to 950, and further preferably 130 to 700. In this case, the value of a is determined by a molecular weight of the polysiloxane compound of the component A.

In the base material of the medical device of the present invention, the component A may be used singly or may be used in combination of two or more.

In the base material of the medical device of the present invention, as other compound copolymerized with the component A, a component B being a polymerizable monomer having a fluoroalkyl group is preferable. The component B has water repellent and oil repellent properties due to reduction in critical surface tension caused by the fluoroalkyl group, and thereby, the effect that reduces contamination of the medical device surface caused by components such as protein and lipid in a body fluid is generated. In addition, the component B has the effect that provides a medical device having flexibility, excellent wearing feeling, and excellent mechanical properties such as folding resistance. Specific preferable examples of the fluoroalkyl group of the component B include fluoroalkyl groups having a carbon number of 1 to 20 such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a pentafluoropropyl group, a tetradecafluorooctyl group, a pentadecafluorooctyl group, an octadecafluorodecyl group, and a nonadecafluorodecyl group. The examples more preferably include fluoroalkyl groups having a carbon number of 2 to 8 such as a trifluoroethyl group, a tetrafluoropropyl group, a hexafluoroisopropyl group, an octafluoropentyl group, and a dodecafluorooctyl group, and most preferably is a trifluoroethyl group A polymerizable functional groups of the component B is preferably a radical polymerizable functional group and more preferably a functional group having a carbon-carbon double bond. Examples of the preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residues, an isocrotonic acid residue, and a citraconic acid residue. Among them, the (meth)acryloyl group is the most preferable functional group because the (meth)acryloyl group is highly polymerizable.

A (meth)acrylic acid fluoroalkyl ester is the most preferable as the component B because this ester has significant effect that provides the medical device having flexibility, excellent wearing feeling, and excellent mechanical properties such as folding resistance. Specific examples of this (meth)acrylic acid fluoroalkyl ester include trifluoroethyl (meth)acrylate, tetrafluoroethyl(meth)acrylate, trifluoropropyl(meth)acrylate, tetrafluoropropyl(meth)acrylate, pentafluoropropyl(meth)acrylate, hexafluorobutyl(meth) acrylate, hexafluoroisopropyl(meth)acrylate, heptafluorobutyl(meth)acrylate, octafluoropentyl(meth) acrylate, nonafluoropentyl(meth)acrylate, dodecafluoropentyl(meth)acrylate, dodecafluoroheptyl(meth)acrylate, dodecafluorooctyl(meth)acrylate, and tridecafluoroheptyl(meth) acrylate. Trifluoroethyl(meth)acrylate, tetrafluoroethyl (meth)acrylate, hexafluoroisopropyl(meth)acrylate, octafluoropentyl(meth)acrylate, and dodecafluorooctyl (meth)acrylate are preferably used. The most preferable is trifluoroethyl(meth)acrylate.

In the base material of the medical device of the present invention, the component B may be used singly or may be used in combination of two or more.

A content of the component B in the copolymer to 100 parts by mass of the component A is preferably 10 to 500 parts by mass, more preferably 20 to 400 parts by mass, and further preferably 20 to 200 parts by mass. When the used amount of the component B is too small, the base material tends to generate white turbidity and have insufficient mechanical properties such as folding resistance.

In addition, as a copolymer used in the base material, a copolymer in which a component different from the component A and the component B (hereinafter referred to as a component C) is further copolymerized in addition to the component A and the component B may be used.

As the component C, a component that lowers a glass transition point of the copolymer to room temperature or to a temperature of 0° C. or less is preferable. Such a component decreases cohesive energy, and therefore, have effect to provide the copolymer with rubber elasticity and softness.

A polymerizable functional groups in the component C is preferably a radical polymerizable functional group and more preferably a functional group having a carbon-carbon double bond. Examples of the preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residues, an isocrotonic acid residue, and a citraconic acid residue. Among them, the (meth)acryloyl group is the most preferable functional group because the (meth)acryloyl group is highly polymerizable.

As the component C, preferable examples for improving flexibility and mechanical properties such as folding resistance include (meth)acrylic acid alkyl esters, preferably (meth)acrylic acid alkyl esters in which a carbon number of the alkyl group is 1 to 20. Specific examples thereof can include methyl(meth)acrylate, ethyl(meth)acrylate, n-propyl (meth)acrylate, n-butyl(meth)acrylate, tert-butyl(meth)acrylate, isobutyl(meth)acrylate, n-hexyl(meth)acrylate, n-octyl (meth)acrylate, 2-ethylhexyl(meth)acrylate, n-heptyl(meth) acrylate, n-nonyl(meth)acrylate, n-decyl(meth)acrylate, isodecyl(meth)acrylate, n-lauryl(meth)acrylate, tridecyl (meth)acrylate, n-dodecyl(meth)acrylate, cyclopentyl(meth) acrylate, cyclohexyl(meth)acrylate, and n-stearyl(meth)acrylate, and more preferably include n-butyl(meth)acrylate, n-octyl(meth)acrylate, n-lauryl(meth)acrylate, and n-stearyl (meth)acrylate. Among them, (meth)acrylic acid alkyl esters in which a carbon number of the alkyl group is 1 to 10 are more preferable. When the carbon number of the alkyl group is too large, transparency of the obtained medical device may be deteriorated, which is not preferable.

In addition, in the base material of the medical device of the present invention, in order to improve mechanical properties, surface wettability, and dimensional stability of the medical device, a monomer (the component C) other than the component A and the component B described below can be copolymerized in accordance with request.

As the monomer (the component C) for improving mechanical properties, for example, aromatic vinyl compound such as styrene, tert-butylstyrene, and α-methyl styrene are included.

As the monomer (the component C) for improving surface wettability, for example, methacrylic acid, acrylic acid, itaconic acid, 2-hydroxyethyl methacrylate, 2-hydroxyethyl acrylate, 2-hydroxypropyl methacrylate, 2-hydroxypropyl acrylate, glycerol methacrylate, polyethylene glycol methacrylate, N,N-dimethyl acrylamide, N-methyl acrylamide, N,N-dimethylaminoethyl methacrylate, methylene-bis-acrylamide, diacetone acrylamide, N-vinylpyrrolidone, N-vinylcaprolactam, N-vinylacetamide, and N-vinyl-N-methylacetamide are included. Among them, the monomer having an amino group or an amide group such as N,N-dimethyl acrylamide, N-methyl acrylamide, N,N-dimethylaminoethyl methacrylate, methylene-bis-acrylamide, diacetone acrylamide, N-vinylpyrrolidone, N-vinylcaprolactam, N-vinylacetamide, and N-vinyl-N-methylacetamide are preferable. Particularly, the monomer having an amino group such as N,N-dimethylaminoethyl methacrylate is preferable from the viewpoint of excellent compatibility with a dye.

As the monomer (the component C) for improving dimensional stability of the medical device, for example, ethylene glycol dimethacrylate, diethylene glycol dimethacrylate, triethylene glycol dimethacrylate, polyethylene glycol dimethacrylate, trimethylolpropane trimethacrylate, pentaerythritol tetramethacrylate, bisphenol A dimethacrylate, vinyl methacrylate, acrylic and methacrylate, and acrylates corresponding to these methacrylate, divinyl benzene, and triallyl isocyanurate are included.

In the base material of the medical device of the present invention, the component C may be used singly or in combination of two or more.

A used amount of the component C to 100 parts by mass of the component A is preferably 0.001 to 400 parts by mass, more preferably 0.01 to 300 parts by mass, further preferably 0.01 to 200 parts by mass, and most preferably 0.01 to 30 parts by mass. When the used amount of the component C is too small, effects which are expected to the component C tend not to be obtained. When the used amount of the component C is too large, the medical device tends to generate white turbidity and have insufficient mechanical properties such as folding resistance.

The medical device of the present invention may further include other components (components Ck) such as an ultraviolet absorber, a dye, a colorant, a wetting agent, a slip agent, pharmaceutical and nutraceutical components, a compatibilizing component, an antimicrobial component, and a release agent. Any of the components described above may be included in the form of a non-reactive component or in the form of a copolymer component. When one or more of the components Ck are used, each of a total used amounts of the components Ck to 100 parts by mass to the composition A is preferably 0.00001 to 100 parts by mass, more preferably 0.0001 to 30 parts by mass, and further preferably 0.001 to 5 parts by mass. When the used amount of the component Ck is too small, expected effects of the component Ck such as ultraviolet absorption and coloring tend not to be sufficiently obtained. When the used amount of the component Ck is too large, the obtained medical device tends to generate white turbidity, which is not preferable.

When the base material of the medical device (particularly, an ophthalmic lens) of the present invention contains an ultraviolet absorber, body tissues of a wearer (an eye in the case of an ophthalmic lens) can be protected from harmful ultraviolet. In addition, when the medical device contains a colorant, the medical device is colored and easily distinguished, and therefore, convenience at the time of handling is improved.

Any of the components described above may be included in the form of a non-reactive component or in the form of a copolymer component. When the component described above is copolymerized, that is, when an ultraviolet absorber having a polymerizable functional group, a colorant having a polymerizable functional group, or the like is used, possibility of elution is reduced since the component is copolymerized to the base material and immobilized, which is preferable.

As an aspect, the base material of the medical device according to the present invention is preferably made of the component (the component Ck) selected from the ultraviolet absorber and the colorant, two or more kinds of the component C, and the component A and the component B. In this case, as the components C, at least a kind of (meth)acrylic acid alkyl ester having a carbon number of 1 to 10 and at least a kind of a monomer for improving the surface wettability are preferably selected. By using two or more kinds of the components C, affinity of the ultraviolet absorber and colorant is improved and a transparent base material can be easily obtained.

When the ultraviolet absorber is used, a used amount thereof to 100 parts by mass of the component A is preferably 0.01 to 20 parts by mass, more preferably 0.05 to 10 parts by mass, and further preferably 0.1 to 2 parts by mass. When the colorant is used, a used amount thereof to 100 parts by mass of the component A is preferably 0.00001 to 5 parts by mass, more preferably 0.0001 to 1 parts by mass, and further preferably 0.0001 to 0.5 parts by mass. When the content of the ultraviolet absorber or the colorant is too small, effect of the ultraviolet absorber or effect of the colorant is difficult to obtain. On the contrary, when the content thereof is too large, it is difficult to make these components dissolve in the base material.

Furthermore, as a copolymer used for the base material, a copolymer in which a component M is further copolymerized in addition to the component A may be used. The component M is a "monofunctional monomer having a polymerizable functional group and a siloxanyl group in one molecule".

In this specification, the siloxanyl group means a group having a Si—O—Si bond.

The siloxanyl group of the component M is preferably a straight-chain. When the siloxanyl group is a straight-chain, a shape recovery property of the obtained medical device is improved. Here, the straight-chain indicates a structure represented by Si—(O—Si)$_{n-1}$—O—Si whose start point is a silicon atom bonded to a group having a polymerizable group and that is sequentially bonded in the form of a line (here, n represents an integer of 2 or more). In order to obtain a sufficient shape recovery property of the obtained medical device, n is preferably an integer of 3 or more, more preferably 4 or more, further preferably 5 or more, and most preferably 6 or more. In addition, "a siloxanyl group being a straight-chain" means that the siloxanyl group has the straight-chain structure and does not have Si—O—Si bonds which do not satisfy the conditions of the straight-chain structure.

A number average molecular weight of the component M is preferably 300 to 120000. When the number average molecular weight of the component M is in this range, a base material having flexibility (low modulus), excellent wearing feeling, and excellent mechanical properties such as folding resistance is obtained. The number average molecular weight of the component M is preferably 500 or more because the base material having mechanical properties such as folding resistance and the shape recovery property is obtained. The number average molecular weight of the component M is more preferably in a range of 1000 to 25000 and further preferably in a range of 5000 to 15000. When the number average molecular weight of the component M is too small, mechanical properties such as folding resistance and the shape recovery property tend to deteriorate, and particularly when the number average molecular weight is less than 500, the folding resistance and the shape recovery property may deteriorate. When the number average molecular weight of the component M is too large, flexibility and transparency tend to deteriorate, which is not preferable.

A polymerizable functional groups in the component M is preferably a radical polymerizable functional group and more preferably a functional group having a carbon-carbon double bond. Examples of the preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residues, an isocrotonic acid residue, and a citraconic acid residue. Among them, the (meth)acryloyl group is the most preferable functional group because the (meth)acryloyl group is highly polymerizable.

As the component M, a component having a structure of the following formula (ML1) is preferable.

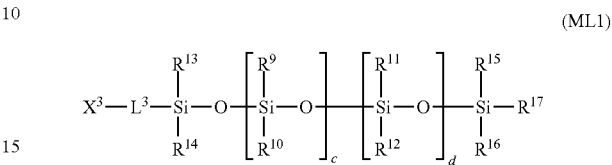

(ML1)

In formula (ML1), $X^3$ represents a polymerizable functional group. $R^9$ to $R^{17}$ each independently represents a substituent selected from hydrogen, an alkyl group having a carbon number of 1 to 20, a phenyl group, and a fluoroalkyl group having a carbon number of 1 to 20. $L^3$ represents a divalent group. c and d each independently represents an integer of 0 to 700. Here, c and d are not zero at the same time.

$X^3$ is preferably a radical polymerizable functional group and more preferably a functional group having a carbon-carbon double bond. Examples of the preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residues, an isocrotonic acid residue, and a citraconic acid residue. Among them, the (meth)acryloyl group is the most preferable functional group because the (meth)acryloyl group is highly polymerizable.

In addition, the polymerizable functional group of the component M is preferably copolymerizable with the polymerizable functional group of the component A because a medical device having excellent mechanical properties is easily obtained, and is more preferably the same as the polymerizable functional group of the component A because a medical device having excellent surface characteristics is easily obtained by uniformly copolymerizing the component M and the component A.

Specific preferable examples of $R^9$ to $R^{17}$ include hydrogen; an alkyl group having a carbon number of 1 to 20 such as a methyl group, an ethyl group, a propyl group, an isopropyl group, a butyl group, a t-butyl group, a decyl group, a dodecyl group, and an octadecyl group; a phenyl group, and a fluoroalkyl group having a carbon number of 1 to 20 such as a trifluoromethyl group, a trifluoroethyl group, a trifluoropropyl group, a tetrafluoropropyl group, a hexafluoroisopropyl group, a pentafluorobutyl group, a heptafluoropentyl group, a nonafluorohexyl group, a hexafluorobutyl group, a heptafluorobutyl group, an octafluoropentyl group, a nonafluoropentyl group, a dodecafluoroheptyl group, a tridecafluoroheptyl group, a dodecafluorooctyl group, a tridecafluorooctyl group, a hexadecafluorodecyl group, a heptadecafluorodecyl group, a tetrafluoropropyl group, a pentafluoropropyl group, a tetradecafluorooctyl group, a pentadecafluorooctyl group, an octadecafluorodecyl group, and a nonadecafluorodecyl group. Among them, from the viewpoint of providing excellent mechanical properties and high oxygen permeability to the medical device, more preferable is hydrogen and the methyl group, and most preferable is the methyl group.

As $L^3$, a divalent group having a carbon number of 1 to 20 is preferable. Among them, groups represented by the following formulae (LE1) to (LE12) are preferable; among them, the groups represented by the following formulae (LE1), (LE3), (LE9) and (LE11) are more preferable; the groups represented by the following formulae (LE1) and (LE3) are further preferable; and the group represented by the following formula (LE1) is the most preferable, because these groups have an advantage that the compound of formula (ML1) is easily obtained in high purity. Here, the following formulae (LE1) to (LE12) are illustrated as an end bonding to the polymerizable functional group $X^3$ is in the left side and an end bonding to silicon atom is in the right side.

$OCH_2CH_2CH_2$ (LE1)

$NHCH_2CH_2CH_2$ (LE2)

$OCH_2CH_2NHCOOCH_2CH_2CH_2$ (LE3)

$OCH_2CH_2NHCONHCH_2CH_2CH_2$ (LE4)

$OCH_2CH_2CH_2CH_2$ (LE5)

$NHCH_2CH_2CH_2CH_2$ (LE6)

$OCH_2CH_2NHCOOCH_2CH_2CH_2CH_2$ (LE7)

$OCH_2CH_2NHCONHCH_2CH_2CH_2CH_2$ (LE8)

$OCH_2CH_2OCH_2CH_2CH_2$ (LE9)

$NHCH_2CH_2OCH_2CH_2CH_2$ (LE10)

$OCH_2CH_2NHCOOCH_2CH_2OCH_2CH_2CH_2$ (LE11)

$OCH_2CH_2NHCONHCH_2CH_2OCH_2CH_2CH_2$ (LE12)

In formula (ML1), c and d each independently represents an integer of 0 to 700. Here, c and d are not zero at the same time. (c+d), which is a total value of c and d, is preferably 3 or more, more preferably 10 or more, more preferably 10 to 500, more preferably 30 to 300, and further preferably 50 to 200.

When all of $R^9$ to $R^{17}$ are methyl groups, d equals to 0, and a is preferably 3 to 700, more preferably 10 to 500, more preferably 30 to 300, and further preferably 50 to 200. In this case, the value of c is determined by a molecular weight of the component M.

In the base material of the medical device of the present invention, the component M may be used singly or may be used in combination of two or more.

The base material of the medical device of the present invention contains an adequate amount of the component M, and thereby, crosslink density is decreased and a degree of freedom of the polymer is increased, and therefore, an adequately soft and low modulus base material can be realized. On the contrary, when the content of the component M is too small, the crosslink density becomes high and the base material becomes stiff. In addition, when the content of the component M is too large, the base material becomes too soft and easily break, which is not preferable.

In the base material of the medical device of the present invention, as a mass ratio of the component M and the component A, the component M is preferably 5 to 200 parts by mass, more preferably 7 to 150 parts by mass, and most preferably 10 to 100 parts by mass to the 100 parts of the component A. When the content of the component M to 100 parts by mass of the component A is less than 5 parts by mass, the crosslink density becomes high and the base material becomes stiff. In addition, when the content of the component M to 100 parts by mass of the component A is more than 200 parts by mass, the base material becomes too soft and easily break, which is not preferable.

In addition, in the base material of the medical device of the present invention, a degree of crosslink is preferably in a range of 2.0 to 18.3. The degree of crosslink is represented by the following formula (Q1).

$$\text{DEGREE OF CROSSLINK} = \frac{\sum_{n=1}^{\infty} \{Qn \times (n-1)\}}{\sum_{n=1}^{\infty} Wn} \quad (Q1)$$

In formula (Q1), Qn represents an amount of total milimol of a monomer having n polymerizable groups per molecule and Wn represents a total mass (kg) of the monomer having n polymerizable groups per molecule. When a molecular weight of the monomer has distribution, the amount of milimol is determined to be calculated using a number average molecular weight.

When the degree of crosslink of the base material of the present invention is less than 2.0, the base material is too soft and handling thereof becomes difficult, whereas, when the degree of crosslink exceeds 18.3, the base material is too stiff and wearing feeling tends to deteriorate, which is not preferable. A more preferable range of the degree of crosslink is 3.5 to 16.0; a further preferable range is 8.0 to 15.0; and the most preferable range is 9.0 to 14.0.

As another aspect, the base material of the medical device of the present invention may be a hydrogel, and preferably a silicone hydrogel containing 5% by mass or more of silicon atoms.

In the medical device according to the present invention, a base material for hydrogel according to another aspect, at least a kind of a component S being a silicon monomer represented by the following general formulae (s1) to (s2) is preferably included as a copolymer component.

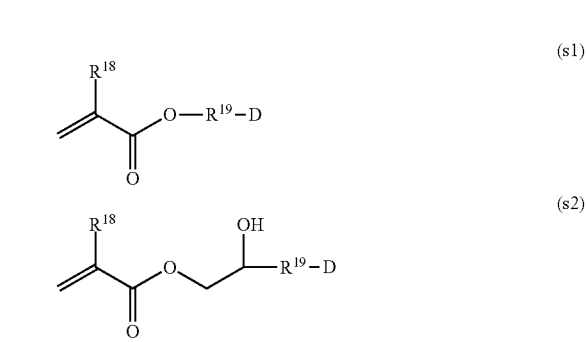

In Formulae (s1) to (s2), $R^{18}$ independently represents hydrogen or a methyl group. $R^{19}$ represents an alkylene group having a carbon number of 1 to 20 or an arylene group having a carbon number of 6 to 20, and a $CH_2$ group in the alkylene group or the arylene group is optionally substituted with —O—, —S—, —CO—, —O—CO—, or —CO—O—. D represents a siloxanyl group.

As preferable example of $R^{19}$, alkylene groups having a carbon number of 1 to 20 optionally having one or more hydroxy group such as a methylene group, an ethylene group, a propylene group, an isopropylene group, a butylene group, a hydroxymethylene group, and a hydroxyethylene group; and arylene groups having a carbon number of 6 to 20 optionally having one or more hydroxy group such as a phenylene group, a tolylene group, a xylylene group, a naphthylene group, and a hydroxyphenylene group are exemplified. Furthermore, the $CH_2$ group in the alkylene group or the arylene group is optionally substituted with —O—, —S—, —CO—, —O—CO—, or by —CO—O—, and, for example, an acetylene group, —$CH_2$—O—$C_3H_6$—, and the like are exemplified. Among them, an alkylene having a carbon number of 2 to 5 and —$CH_2$—O—$C_3H_6$— are preferable and a propylene group and —$CH_2$—O—$C_3H_6$— are more preferable in that the silicone hydrogel easily satisfies both low modulus and transparency.

A preferable example of D is a siloxanyl group represented by the following formulae (d1) to (d3).

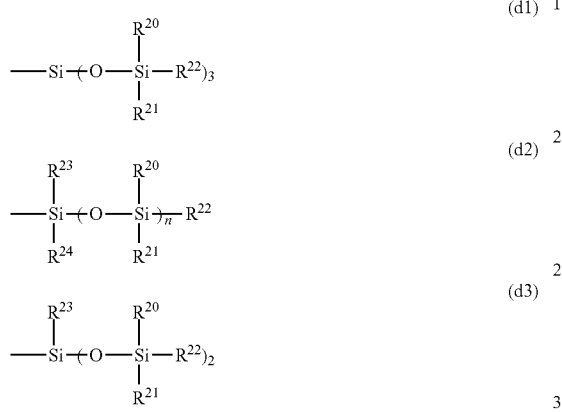

In formulae (d1) to (d3), $R^{20}$ to $R^{24}$ each independently represent a substituent selected from an alkyl group having a carbon number of 1 to 20 such as a methyl group, an ethyl group, a propyl group, and an isopropyl group or a substituent selected from an aryl group having a carbon number of 6 to 20 such as a phenyl group, a naphthyl group, and an anthracenyl group. n represents an integer of 1 to 50, and 2 to 20 is more preferable, and 3 to 8 is the most preferable in that the silicone hydrogel satisfies both transparency and high oxygen permeability.

The component S is preferably silicone monomers represented by the following formulae (t1) to (t4). The base material of the present invention preferably include at least one component S being silicone monomers represented by the following formulae (t1) to (t4) as a copolymer component. In the medical device according to the present invention, a base material for hydrogel according to another aspect, the component S may be used singly or in combination of two or more.

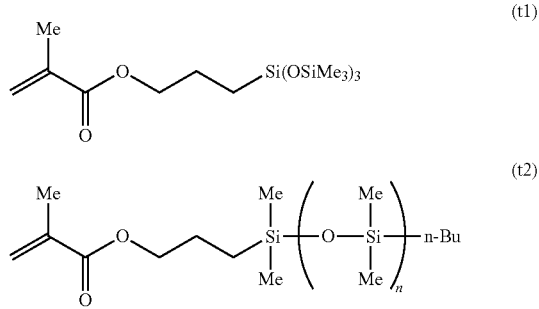

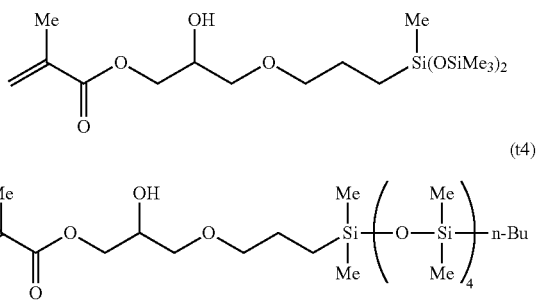

In the above formula (t2), n represents an integer of 3 to 200 (a mass average molecular weight of about 500 to 15000).

A preferable example of the component S is acrylamide-based silicone monomers disclosed in Japanese Translation of PCT Application No. 2007-526364 and Japanese Patent Application Laid-open No. 10-212355.

In addition, in the medical device according to the present invention, the base material for hydrogel according to another aspect includes a hydrophilic component H as a copolymer component.

As a polymerizable functional groups in the hydrophilic component H is preferably a radical polymerizable functional group and more preferably a functional group having a carbon-carbon double bond. Examples of the preferable polymerizable functional group include a vinyl group, an allyl group, a (meth)acryloyl group, an α-alkoxymethylacryloyl group, a maleic acid residue, a fumaric acid residue, an itaconic acid residue, a crotonic acid residues, an isocrotonic acid residue, and a citraconic acid residue. Among them, the (meth)acryloyl group is the most preferable because the (meth)acryloyl group is highly polymerizable.

Preferable examples of the hydrophilic component H include methacrylic acid, acrylic acid, itaconic acid, 2-hydroxyethyl methacrylate, 2-hydroxyethyl acrylate, 2-hydroxypropyl methacrylate, 2-hydroxypropyl acrylate, glycerol methacrylate, polyethylene glycol methacrylate, N,N-dimethyl acrylamide, N-methyl acrylamide, dimethylaminoethyl methacrylate, methylene-bis-acrylamide, diacetone acrylamide, N-vinylpyrrolidone, N-vinylcaprolactam, N-vinylacetamide, and N-vinyl-N-methylacetamide. Among them, the monomer having an amide group such as N,N-dimethyl acrylamide, N-methyl acrylamide, dimethylaminoethyl methacrylate, methylene-bis-acrylamide, diacetone acrylamide, N-vinylpyrrolidone, N-vinylcaprolactam, N-vinylacetamide, and N-vinyl-N-methylacetamide are preferable from the viewpoint of a highly hydrophilic property, and N,N-dimethyl acrylamide is the most preferable from the viewpoint of compatibility with the component S.

In the medical device according to the present invention, the base material for the hydrogel according to another aspect preferably further includes a cross-linkable component I having two or more of polymerizable groups in one molecule. Preferable examples of the cross-linkable component I include ethylene glycol dimethacrylate, diethylene glycol dimethacrylate, triethylene glycol dimethacrylate, polyethylene glycol dimethacrylate, trimethylolpropane trimethacrylate, pentaerythritol tetramethacrylate, bisphenol A dimethacrylate, vinyl methacrylate, acryl methacrylate, and acrylates corresponding to these methacrylates, divinyl benzene, and triallyl isocyanurate.

An amount of the hydrophilic component H to 100 parts by mass of the component S is preferably 20 to 300 parts by mass, more preferably 25 to 200 parts by mass, further preferably 30 to 150 parts by mass, and most preferably 30 to 80 parts by mass. When the used amount of the hydrophilic component H is too small, a water content of the base material becomes low and the base material becomes stiff. When the used amount of the hydrophilic component is too large, the base material tends to have white turbidity and deteriorate dimension stability due to increase in evaporation of water from the base material surface.

A used amount of the cross-linkable component 1 to 100 parts by mass of the component S is preferably 0.01 to 20 parts by mass, more preferably 0.05 to 10 parts by mass, further preferably 0.1 to 5 parts by mass, and most preferably 0.5 to 4 parts by mass. When the amount of the cross-linkable component I is too small, shape stability of the base material deteriorates. When the amount of the cross-linkable component is too large, the base material becomes stiff, and thus, wearing feeling becomes worse particularly when the medical device is used as a soft ophthalmic lens.

In the medical device according to the present invention, the base material for hydrogel according to another aspect may further include components (components Ck) such as an ultraviolet absorber, a dye, a colorant, a wetting agent, a slip agent, pharmaceutical and nutraceutical components, a compatibilizing component, an antimicrobial component, and a release agent. Any of the components described above may be included in the form of a non-reactive component or in the form of a copolymer component.

When one or more of the components Ck are used, each of a total used amounts of the components Ck to 100 parts by mass of the composition S is preferably 0.00001 to 100 parts by mass, more preferably 0.0001 to 30 parts by mass, and further preferably 0.001 to 5 parts by mass. When the used amount of the component Ck is too small, expected effects of the component Ck such as ultraviolet absorption and coloring tend not to be sufficiently obtained. When the used amount of the component Ck is too large, the obtained medical device tends to generate white turbidity, which is not preferable.

When the base material for hydrogel contains an ultraviolet absorber, body tissues of a wearer (an eye in the case of an ophthalmic lens) can be protected from harmful ultraviolet. In addition, when the surface contains a colorant, the medical device is colored and the medical device is easy to be distinguished, and therefore, convenience at the time of handling is improved.

Any of the components described above may be included in the form of a non-reactive component or in the form of a copolymer component. When the component described above is copolymerized, that is, when an ultraviolet absorber having a polymerizable functional group, a colorant having a polymerizable functional group, or the like is used, possibility of elution is reduced because the component is copolymerized to the base material and immobilized, which is preferable.

The base material for hydrogel preferably includes components (components Ck) selected from the ultraviolet absorber and the colorant.

When the ultraviolet absorber is used, a used amount thereof to 100 parts by mass of the component S is preferably 0.01 to 20 parts by mass, more preferably 0.05 to 10 parts by mass, and further preferably 0.1 to 5 parts by mass. When the colorant is used, a used amount thereof to 100 parts by mass of the component S is preferably 0.00001 to 5 parts by mass, more preferably 0.0001 to 1 parts by mass, and further preferably 0.0001 to 0.5 parts by mass. When the content of the ultraviolet absorber or the colorant is too small, effect of the ultraviolet absorber or effect of the colorant is difficult to obtain. On the contrary, when the content thereof is too large, it is difficult to make these components dissolve in the base material.

As a method for producing the base material of the medical device, that is, a lens-shaped or sheet-like molding, known methods can be used. For example, a method in which a rod or a plate-like polymer is obtained and the polymer is processed in a desired shape by a cutting process or the like, a mold polymerization method, a spin casting method, and the like can be used. When the medical device is obtained by the cutting process, a freezing cutting under low temperature is preferable.

As one example, a method for producing an ophthalmic lens by polymerizing a raw material composition of the base material using the mold polymerization method will be described below. First, the raw material composition is filled into a gap of two mold members having a certain shape. As a material for the mold members, a resin, a glass, a ceramic, a metal, and the like are included. An optically transparent material is preferably when photopolymerization is carried out, and therefore, a resin or a glass is preferably used. Depending on a shape of the mold members and properties of the raw material composition, a gasket may be used in order to provide a constant thickness to an ophthalmic lens and prevent liquid leakage of the raw material composition filled in the gap. Subsequently, the mold of which the raw material composition is filled in the gap is irradiated with active rays such as ultraviolet rays, visible light rays, or combination thereof, or is heated in an oven or a liquid bath to polymerize the filled raw material composition. These two polymerization methods may be used together at the same time. In other words, the heat polymerization may be carried out after the photopolymerization or the photopolymerization may be carried out after the heat polymerization. As a specific aspect of the photopolymerization, for example, the raw material composition is irradiated with light including ultraviolet rays such as light of a mercury lamp or a ultraviolet lamp (for example, FL15B, TOSHIBA CORPORATION) for a short time (usually, 1 hour or less). When the heat polymerization is carried out, conditions in which temperature of the composition gradually rises from room temperature and the temperature is raised to 60° C. to 200° C. for several hours to several tens of hours is preferable in order to maintain optical uniformity and quality of an ophthalmic lens and improve repeatability.

In the polymerization, a heat polymerization initiator or a photopolymerization initiator represented by a peroxide or an azo compound is preferably added in order to facilitate the polymerization. When the heat polymerization is carried out, the initiator having optimum decomposition properties at a desired reaction temperature is selected. In general, an azo initiator and a peroxide initiator having a 10-hour half-life temperature of 40° C. to 120° C. are preferable. As a photoinitiator when the photopolymerization is carried out, a carbonyl compound, a peroxide, an azo compound, a sulfur compound, a halogen compound, and a metal salt may be included. These polymerization initiators may be used singly or in combination. An amount of the polymerization initiator is preferably up to 5% by mass at maximum to the raw material composition.

When the polymerization is carried out, a polymerization solvent can be used. Various organic or inorganic solvents are applicable as the solvent. Examples of the solvents include water; alcohols such as methyl alcohol, ethyl alcohol, normal propyl alcohol, isopropyl alcohol, normal butyl alcohol, isobutyl alcohol, t-butyl alcohol, t-amyl alcohol, tetrahydrolinalool, ethylene glycol, diethylene glycol, triethylene glycol, tetraethylene glycol and polyethylene glycol; glycol ether-based solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, and polyethylene glycol dimethyl ether; ester-based solvent such as ethyl acetate, butyl acetate, amyl acetate, ethyl lactate, and methyl benzoate; aliphatic hydrocarbon solvents such as normal-hexane, normal-heptane, and normal-octane; alicyclic hydrocarbon solvents such as cyclohexane and ethylcyclohexane; ketone-based solvents such as acetone, methyl ethyl ketone; and methyl isobutyl ketone; aromatic hydrocarbon solvents such as benzene, toluene, and xylene; and petroleum-based solvent. These solvents may be used singly or in combination of two or more.

The medical device of an embodiment of the present invention requires that a layer made of an acidic polymer and a basic polymer is formed (hereinafter, referred to as a coating layer) on at least a part of the surface of the base material produced as described above. By having the coating layer, excellent wettability and lubricity are provided on the surface of the medical device, and therefore, excellent wearing feeling can be provided.

The inventors of the present invention have found that a medical device that reduces a risk of bacterial proliferation and has excellent lubricity and wettability in a low water content base material can be provided by forming a coating layer made of an acidic polymer and a basic polymer on the base material surface of the medical device of the present invention made by treating with a solution of at least a kind of multi-component copolymer of three or more components. In addition, the inventors of the present invention also have found that the medical device that reduces lipid adhesion in a water containing hydrogel base material, particularly a silicone hydrogel base material.

The coating layer of the medical device of the present invention does not need to have a covalent bond between the coating layer and the base material. Because the production can be carried out by a simple process, it is preferable that the coating layer does not have a covalent bond between the base material and the coating layer. Without having a covalent bond between the base material and the coating layer, the coating layer has a practical durability.

The coating layer is formed by treating the surface of the base material with an acidic polymer solution (the "solution" means an aqueous solution) and a basic polymer solution (the "solution" means an aqueous solution) that are described below in detail. Here, the aqueous solution is a solution in which water is a main component.

The acidic polymer solution and the basic polymer solution of the present invention generally mean solutions including a kind of polymer (a kind means a polymer group in which the same monomers constitute the polymer. A polymer synthesized in different formulation ratio is not a kind even if the same monomers constitute the polymer). Even when a solution contains a kind (the same) of a polymer, solutions having different concentrations are not assumed as a kind.

The coating layer is preferably formed from one or more kinds of the acidic polymers and one or more kinds of the basic polymers. When two or more kinds of the acidic polymers or two or more kinds of the basic polymers are used, properties such as lubricity and antifouling properties are easily developed on the surface of the medical device, which is more preferable. The tendency is particularly enhanced when the two or more kinds of the acidic polymers and one or more kinds of the basic polymers are used, which is further preferable.

The coating layer is preferably formed by carrying out treatment with one or more kinds of the acidic polymer solutions one or more times, and treatment with one or more kinds of the basic polymer solutions one or more times.

The coating layer is formed on the surface of the base material by carrying out treatment with one or more kinds of the acidic polymer solutions and treatment with one or more kinds of the basic polymer solutions preferably each one to five times, more preferably each one to three times, and further preferably each one to two times. The number of times of treatment with the acidic polymer solution and the number of times of treatment with the basic polymer solution may be different.

The coating layer is preferably formed on the surface of the base material by carrying out the treatment with one or more kinds of the acidic polymer solutions one or two times and treatment with one or more kinds of the basic polymer solutions one or two times, and consequently, carrying out the treatment three times in total.

The inventors of the present invention have found that, in the medical device of the present invention, two or three times in total of the treatment with one or more kinds of the acidic polymer solutions and the treatment with one or more kinds of the basic polymer solutions, which are extremely low times, excellent wettability and lubricity can be provided. From the viewpoint of shortening in production processes, this has significantly important meaning in industry. In this sense, in the medical device of the present invention, total times of the treatment with the acidic polymer solution and the treatment with the basic polymer solution is preferably two or three times.

For the coating layer according to the medical device of the present invention, to carry out the treatment with two kinds of the acidic polymer solutions one time each and treatment with the basic polymer solution one time is preferable.

The inventors of the present invention have ascertained that development of wettability and lubricity are hardly observed in the coating layer in which only treatment with either the acidic polymer solution or the basic polymer solution is carried out.

As the acidic polymer used for the coating layer of the present invention, a homopolymer or a copolymer having a plurality of groups having acidity along the polymer chain can be preferably used. As the group having acidity, a carboxy group, a sulfonic acid group, a phosphoric acid group, and salts thereof are preferable, and the carboxy group and the salt thereof are the most preferable. For example, preferable examples of such an acidic homopolymer include polymethacrylic acid, polyacrylic acid, poly(vinylbenzoic acid), poly(thiophene-3-acetic acid), poly(4-styrenesulfonic acid), polyvinylsulfonic acid, poly(2-acrylamide-2-methylpropanesulfonic acid) and salts thereof.

When the acidic polymer is a copolymer, a copolymer including a monomer having one or more groups having acidity and polymerizable group in one molecule (hereinafter referred to as an acidic monomer) is preferable. As the acidic monomer, a monomer having an allyl group, a vinyl group, and a (meth)acryloyl group as a polymerizable functional group is preferable from the viewpoint of highly polymerizable property, and the monomer having the (meth)acryloyl group is the most preferable. As preferable acidic monomers constituting the copolymer, (meth)acrylic acid, vinylbenzoic acid, styrenesulfonic acid, vinylsulfonic acid, 2-acrylamide-2-methylpropanesulfonic acid, itaconic acid, allylsulfonic acid, and salts thereof can be exemplified. Among them, (meth)acrylic acid, 2-acrylamide-2-methylpropanesulfonic acid, and the salts thereof are more preferable and (meth) acrylic acid and the salt thereof are the most preferable. As the acidic polymer used in the coating layer of the present invention, a copolymer using two or more kinds of the acidic monomer selected from the above acidic monomers can be used.

The acidic polymer used in the coating layer of the present invention is preferably a copolymer of the above acidic monomer and the monomer having a hydroxy group. When the copolymer of the monomer having a hydroxy group and the acidic monomer is used as the coating layer, the risk of the bacterial proliferation can be reduced because the antifouling property to a lacrimal fluid can be improved. The monomer having a hydroxy group means a monomer having one or more hydroxy group and a radically polymerizable functional group in one molecule. The radically polymerizable functional group is preferably a functional group having a carbon-carbon double bond, and examples of the radically polymerizable functional group include a vinyl group, an allyl group, a (meth)acryloyl group, an α-alkoxymethylacryloyl group, a maleic acid residue, a fumaric acid residue, an itaconic acid residue, a crotonic acid residues, an isocrotonic acid residues, and a citraconic acid residue, and, in terms of ease of polymerization, the monomer having the (meth)acryloyl groups is preferable.

Preferable examples of the monomer having a hydroxy group include hydroxyethyl(meth)acrylate, hydroxypropyl(meth)acrylate, hydroxybutyl(meth)acrylate, hydroxyethyl(meth)acrylamide, glycerol(meth)acrylate, caprolactone modified-2-hydroxyethyl(meth)acrylate, N-(4-hydroxyphenyl)maleimide, hydroxystyrene, and vinyl alcohol (a carboxylic acid vinyl ester as a precursor). As the monomer having a hydroxy group, hydroxyethyl(meth)acrylate, hydroxypropyl(meth)acrylate, and glycerol(meth)acrylate are preferable and, among them, hydroxyethyl(meth)acrylate is the most preferable.

Preferable specific examples of the copolymer of the acidic monomer and the monomer having a hydroxy group include a (meth)acrylic acid/hydroxyethyl(meth)acrylate copolymer, a (meth)acrylic acid/glycerol(meth)acrylate copolymer, a 2-acrylamide-2-methylpropanesulfonic acid/hydroxyethyl (meth)acrylate copolymer, and a 2-acrylamide-2-methylpropanesulfonic acid/glycerol(meth)acrylate copolymer. The (meth)acrylic acid/hydroxyethyl(meth)acrylate copolymers are the most preferable.

As polymers exerting similar effect to the copolymer of the acidic monomer and the monomer having a hydroxy group, polymers having a functional group having acidity and a hydroxy group are exemplified, and for example, when a polysaccharide having an acidic group such as hyaluronic acid, chondroitin sulfate, carboxymethyl cellulose, and carboxypropyl cellulose is used as the coating layer, the antifouling property for the lacrimal fluid can be improved.

The acidic polymer used in the coating layer of the present invention is preferably a copolymer of the above acidic monomer and the monomer having an amide group. When a copolymer of the monomer having an amide group and the acidic monomer are used as the coating layer, wettability and lubricity can be improved because the copolymer can improve a hydrophilic property compared with the homopolymer of the acidic monomer. The monomer having an amide group means a monomer having one or more amide group and radically polymerizable functional group in one molecule. The radically polymerizable functional group is preferable a functional group having a carbon-carbon double bond, and examples of the radically polymerizable functional group include a vinyl group, an allyl group, a (meth)acryloyl group, an α-alkoxymethyl acryloyl group, a maleic acid residue, a fumaric acid residue, an itaconic acid residue, a crotonic acid residues, an isocrotonic acid residues, and a citraconic acid residue, and, in terms of ease of polymerization, the monomer having the (meth)acrylamide groups or N-vinylcarboxylic acid amide (including a cyclic amide) are preferable.

Preferable examples of the monomer having an amide group include N-vinylpyrrolidone, N-vinylcaprolactam, N-vinylacetamide, N-methyl-N-vinylacetamide, N-vinylformamide, N,N-dimethylacrylamide, N,N-diethylacrylamide, N-isopropylacrylamide, N-(2-hydroxyethyl)acrylamide, acryloylmorpholine, and acrylamide. Among the monomers having an amide group, N-vinylpyrrolidone and N,N-dimethylacrylamide are preferable, and N,N-dimethylacrylamide is the most preferable.

Preferable examples of the copolymer of the acidic monomer and the monomer having an amide group include a (meth)acrylic acid/N-vinylpyrrolidone copolymer, a (meth) acrylic acid/N,N-dimethylacrylamide copolymer, a 2-acrylamide-2-methylpropanesulfonic acid/N-vinylpyrrolidone copolymer, and a 2-acrylamide-2-methylpropanesulfonic acid/N,N-dimethylacrylamide copolymer. The most preferable is the (meth)acrylic acid/N,N-dimethylacrylamide copolymer. As polymers exerting similar effect to the copolymer of the acidic monomer and the monomer having an amide group, polymers having a functional group having acidity and an amide group are exemplified, and for example, sialic acid can be included.

When the copolymer of two components of the acidic monomer and another monomer is used, a copolymerization ratio of these [Number of moles of acidic monomer]/[Number of moles of another monomer] is preferably 1/99 to 99/1, more preferably 2/98 to 90/10, and further preferably 10/90 to 80/20. When the copolymerization ratio is in this range, functions such as the lubricity and the antifouling property to the lacrimal fluid can be easily developed.

The acidic polymer used in the coating layer of the present invention is preferably a multi-component copolymer containing three or more components. When the multi-component copolymer is used, when [Total number of moles of acidic monomer]/[Total number of moles of monomers other than acidic monomer] is too small, adhering property of the coating layer is deteriorated, whereas, when the ratio is too large, effects of the antifouling properties and the water solubility, which are expected to other monomers, is deteriorated, and therefore, the ratio is preferably 2/1 to 1/9, more preferably 1/1 to 1/7, and further preferably 1/1 to 1/5. A preferable copolymerization ratio when the monomers other than the acidic monomer in the multi-component copolymer are divided into water soluble monomers and water insoluble monomers is, because water solubility of the multi-component copolymer is deteriorated when [Total number of moles of water insoluble monomer]/[Total number of moles of water soluble monomer] is too large, preferably 0/1 to 4/1, more preferably 0/1 to 1/1, and most preferably 0/1 to 1/4. Here, the "water soluble monomer" in the present invention represents a monomer that exhibits homogeneous appearance without separation when water and the monomer in a ratio of 1:1 are mixed at room temperature and, after stirring, the mixture was left to stand for 1 minute or more, whereas the "water insoluble monomer" represents a monomer that is separated from water under the conditions described above. When the copolymerization ratio of three or more monomers is in this range, functions such as the lubricity and the antifouling property to the lacrimal fluid are easily developed.

The acidic polymer used for the coating layer of the present invention is further preferably a copolymer of three components of the acidic monomer, the monomer having a hydroxy group, and the monomer having an amide group. When the copolymer of three components of the acidic monomer, the monomer having a hydroxy group, and the monomer having an amide group is used as the coating layer, the risk of the bacterial proliferation can be reduced by improving the antifouling property as well as wettability and lubricity can be improved.

Specific preferable examples of the copolymer of three components of the acidic monomer, the monomer having a hydroxy group, and the monomer having an amide group include a (meth)acrylic acid/hydroxyethyl(meth)acrylate/N-vinylpyrrolidone copolymer, a (meth)acrylic acid/hydroxyethyl(meth)acrylate/N,N-dimethylacrylamide copolymer, a (meth)acrylic acid/glycerol(meth)acrylate/N-vinylpyrrolidone copolymer, a (meth)acrylic acid/glycerol(meth)acrylate/N,N-dimethylacrylamide copolymer, a 2-acrylamide-2-methylpropanesulfonic acid/hydroxyethyl(meth)acrylate/N-vinylpyrrolidone copolymer, and a 2-acrylamide-2-methylpropanesulfonic acid/hydroxyethyl(meth)acrylate/N,N-dimethylacrylamide copolymer. The most preferable is the (meth)acrylic acid/hydroxyethyl(meth)acrylate/N,N-dimethylacrylamide copolymer.

When the copolymer of three components of the acidic monomer, the monomer having a hydroxy group, and the monomer having an amide group is used, the adhering property of the coating layer is deteriorated when [Number of moles of acidic monomer]/{[Number of moles of monomer having a hydroxy group]+[Number of moles of monomer having an amide group]} is too small, whereas effect of the antifouling property, which is expected to the monomer having a hydroxy group and the monomer having an amide group, is deteriorated when the ratio is too large, and therefore, the ratio is preferably 2/1 to 1/9, more preferably 1/1 to 1/7, and further preferably 1/1 to 1/5. When [Number of moles of monomer having a hydroxy group]/[Number of moles of monomer having an amide group] in the copolymer of three components is too small, a sufficient antifouling property is not obtained, whereas, when the ratio is too large, water solubility is deteriorated, and therefore, the ratio is preferably 5/1 to 1/5, more preferably 3/1 to 1/4, and most preferably 1/1 to 1/3. When the copolymerization ratio of the copolymer of three components is in this range, functions such as the lubricity and the antifouling property to the lacrimal fluid are easily developed.

Another preferable aspect of the acidic polymer used for the coating layer of the present invention is a copolymer of three components of the acidic monomer and two kinds of monomers having an amide group. In the case of using the copolymer of three components, when [Number of moles of acidic monomer]/[Total number of moles of two monomers having amide groups] is too small, adhesion of the coating layer is deteriorated, whereas, when the ratio is too large, effects of the antifouling property and the water solubility, which is expected to the monomer having an amide group, are deteriorated, and therefore, the ratio is preferably 2/1 to 1/9, more preferably 1/1 to 1/7, and further preferably 1/1 to 1/5. In addition, a preferable copolymerization ratio of the two monomers having an amide group in the copolymer of three components is preferably 1/99 to 99/1, more preferably 10/90 to 90/10, and most preferably 20/80 to 80/20, because a sufficient antifouling property and the water solubility may not be obtained when [Number of moles of monomer having an amide group]/[Number of moles of two monomers having amide groups] is too small or too large. When the copolymerization ratio of the copolymer of three components is in this range, functions such as the lubricity and the antifouling property to the lacrimal fluid are easily developed.

Another preferable aspect of the acidic polymer used for the coating layer of the present invention is a copolymer of four or more components. When [Number of moles of acidic monomer]/[Total number of moles of monomers other than acidic monomer] in the case of using the copolymer of four or more components is too small, adhesion of the coating layer is deteriorated, whereas, when the ratio is too large, effects of the antifouling property and the water solubility, which is expected to the other monomer, are deteriorated, and therefore, the ratio is preferably 2/1 to 1/9, more preferably 1/1 to 1/7, and further preferably 1/1 to 1/5. A preferable copolymerization ratio when the monomers other than the acidic monomer in the multi-component copolymer of four components or more are divided into water soluble monomers and water insoluble monomers is preferably 0/1 to 4/1, more preferably 0/1 to 1/1, and most preferably 0/1 to 1/4 because water solubility of the multi-component copolymer is deteriorated when [Total number of moles of water insoluble monomers]/[Total number of moles of water soluble monomers] is too large. When a copolymerization ratio of four or more monomers is in this range, functions such as the lubricity and the antifouling property to the lacrimal fluid are easily developed.

As the basic polymer used for the coating layer of the present invention, a homopolymer or a copolymer having a plurality of groups having basicity along the polymer chain can be preferably used. As the group having basicity, an amino group and a salt thereof are preferable. For example, preferable examples of the basic homopolymer include amino group-containing (meth)acrylate polymers such as poly(allylamine), poly(vinylamine), poly(ethyleneimine), poly(vinylbenzyltrimethylamine), polyaniline, poly(aminostyrene), poly(N,N-dialkylaminoethyl methacrylate), amino group-containing (meth)acrylamide polymers such as poly(N,N-dimethylaminopropyl acrylamide), and salts thereof.

When the basic polymer is a copolymer, a copolymer including a monomer having one or more of a group having basicity and polymerizable functional group in one molecule (hereinafter referred to as a basic monomer) is preferable. As the basic monomer constituting the copolymer, a monomer having an allyl group, a vinyl group, and a (meth)acryloyl group as a polymerizable functional group is preferable in terms of high polymerizable property, and the monomer having the (meth)acryloyl group is the most preferable. As preferable basic monomers constituting the copolymer, allylamine, vinylamine (N-vinylcarboxylic acid amide as a precursor), vinylbenzyltrimethylamine, amino group-containing styrene, amino group-containing (meth)acrylate, amino group-containing (meth)acrylamide, and salts thereof can be exemplified. Among them, amino group-containing (meth)acrylate, amino group-containing (meth)acrylamide, and the salts thereof are more preferable in terms of high polymerization property, and N,N-dimethylaminoethyl methacrylate, N,N-dimethylaminopropyl acrylamide, and the salts thereof are the most preferable. As the basic polymer used in the coating layer of the present invention, a copolymer using two or more kinds of the basic monomer selected from the above basic monomers can be used.

The basic polymer may be a polymer having a quaternary ammonium structure. When the polymer compound having the quaternary ammonium structure is used for coating of the medical device, an antimicrobial property can be provided to the medical device.

The basic polymer used in the coating layer of the present invention is preferably a copolymer of the above basic monomer and the monomer having a hydroxy group. When the copolymer of the monomer having a hydroxy group and the basic monomer is used as the coating layer, the risk of the bacterial proliferation can be reduced because the antifouling property to body fluids such as the lacrimal fluid can be improved.

Preferable specific examples of the copolymer of the basic monomer and the monomer having a hydroxy group include an N,N-dimethylaminoethyl methacrylate/hydroxyethyl(meth)acrylate copolymer, an N,N-dimethylaminoethyl methacrylate/glycerol(meth)acrylate copolymer, N,N-dimethylaminopropyl acrylamide/hydroxyethyl(meth)acrylate copolymer, and an N,N-dimethylaminopropyl acrylamide/glycerol(meth)acrylate copolymer. The most preferable is the N,N-dimethylaminoethyl methacrylate/hydroxyethyl(meth)acrylate copolymer.

As polymers exerting similar effect to the copolymer of the basic monomer and the monomer having a hydroxy group, aminopolysaccharides such as chitin, which are polymers having a functional group having basicity and a hydroxy group, can be included.

The basic polymer used in the coating layer of the present invention is preferably a copolymer of the above basic monomer and the monomer having an amide group. When a copolymer of the monomer having an amide group and the basic monomer are used as the coating layer, wettability and lubricity can be improved because the copolymer can improve a hydrophilic property compared with the homopolymer of the basic monomer.

Preferable specific examples of the copolymer of the basic monomer and the monomer having an amide group include an N,N-dimethylaminoethyl methacrylate/N-vinylpyrrolidone copolymer, an N,N-dimethylaminoethyl methacrylate/N,N-dimethylacrylamide copolymer, an N,N-dimethylaminopropyl acrylamide/N-vinylpyrrolidone copolymer, and an N,N-dimethylaminopropyl acrylamide/N,N-dimethylacrylamide copolymer. The most preferable is the N,N-dimethylaminopropyl acrylamide/N,N-dimethylacrylamide copolymer.

When a copolymer of two components of the basic monomer and another monomer is used, a copolymerization ratio of these [Number of moles of basic monomer]/[Number of moles of another monomer] is preferably 1/99 to 99/1, more preferably 2/98 to 90/10, and further preferably 10/90 to 80/20. When the copolymerization ratio is in this range, functions such as lubricity and an antifouling property to a lacrimal fluid can be easily developed.

As polymers exerting similar effect to the copolymer of the basic monomer and the monomer having an amide group, partially hydrolyzed chitosan, which is a polymer having a functional group having basicity and an amide group, can be included.

The basic polymer used for the coating layer of the present invention is preferably a multi-component copolymer of three or more components. When the multi-component copolymer is used, when [Total number of moles of basic monomer]/[Total number of moles of monomers other than basic monomer] is too small, adhering property of the coating layer is deteriorated, whereas, when the ratio is too large, effects of the antifouling property and water solubility, which are expected to other monomers are deteriorated, and therefore, the ratio is preferably 2/1 to 1/9, more preferably 1/1 to 1/7, and further preferably 1/1 to 1/5. A preferable copolymerization ratio when the monomers other than the basic monomer in the multi-component copolymer of three or more components are divided into water soluble monomers and water insoluble monomers is preferably 0/1 to 1/5, more preferably 0/1 to 1/4, and most preferably 5/1 to 1/3 because water solubility of the multi-component copolymer is deteriorated when [Total number of moles of water insoluble monomers]/[Total number of moles of water soluble monomers] is too large. Here, the "water soluble monomer" in the present invention represents a monomer that exhibits homogeneous appearance without separation when water and the monomer in a volume ratio of 1:1 are mixed at room temperature and, after stirring, the mixture was left to stand for 1 minute or more, whereas the "water insoluble monomer" represents a monomer that is separated from water under the conditions described above. When the copolymerization ratio of three or more monomers is in this range, functions such as the lubricity and the antifouling property to the lacrimal fluid are easily developed.

The basic polymer used for the coating layer of the present invention is further preferably a copolymer of three components of the basic monomer, the monomer having a hydroxy group, and the monomer having an amide group. When the copolymer of three components of the basic monomer, the monomer having a hydroxy group, and the monomer having an amide group is used as the coating layer, the risk of the bacterial proliferation can be reduced by improving the antifouling property as well as wettability and lubricity can be improved.

Preferable specific examples of the copolymer of three components of the basic monomer, the monomer having a hydroxy group, and the monomer having an amide group include an N,N-dimethylaminoethyl methacrylate/hydroxyethyl(meth)acrylate/N-vinylpyrrolidone copolymer, an N,N-dimethylaminoethyl methacrylate/hydroxyethyl(meth)acrylate/N,N-dimethylacrylamide copolymer, an N,N-dimethylaminoethyl methacrylate/glycerol(meth)acrylate/N-vinylpyrrolidone copolymer, an N,N-dimethylaminoethyl methacrylate/glycerol(meth)acrylate/N,N-dimethylacrylamide copolymer, an N,N-dimethylaminopropyl acrylamide/hydroxypropyl(meth)acrylate/N-vinylpyrrolidone copolymer, and an N,N-dimethylaminopropyl acrylamide/hydroxypropyl(meth)acrylate/N,N-dimethylacrylamide copolymer. The most preferable is the N,N-dimethylaminopropyl acrylamide/hydroxypropyl(meth)acrylate/N,N-dimethylacrylamide copolymer.

When a terpolymer of a basic monomer, a monomer having a hydroxy group, and a monomer having an amide group is used, the adhering property of the coating layer is deteriorated when a copolymerization ratio of these [Number of moles of basic monomer]/{[Number of moles of monomer having a hydroxy group]+[Number of moles of monomer having an amide group]} is too small, whereas effect of the antifouling properties, which is expected to the monomer having a hydroxy group and the monomer having an amide group, is deteriorated when the ratio is too large, and therefore, the ratio is preferably 2/1 to 1/9, more preferably 1/1 to 1/7, and further preferably 1/1 to 1/5. When [Number of moles of monomer having a hydroxy group]/[Number of moles of monomer having an amide group] in the terpolymer is too small, sufficient antifouling properties are not obtained, whereas, when the ratio is too large, the water solubility is deteriorated, and therefore, the ratio is preferably 5/1 to 1/5, more preferably 3/1 to 1/4, and most preferably 1/1 to 1/3. When the copolymerization ratio of the terpolymer is in this range, functions such as the lubricity and the antifouling properties to the lacrimal fluid are easily developed.

Another preferable aspect of the basic polymer used for the coating layer of the present invention is a copolymer of three components of the basic monomer and two kinds of monomers having an amide group. In the case of using the copolymer of three components, when [Number of moles of basic monomer]/[Total number of moles of two monomers having amide groups] is too small, the adhering property of the coating layer is deteriorated, whereas, when the ratio is too large, effects of the antifouling property and the water solubility, which are expected to the monomer having an amide group, are deteriorated, and therefore, the ratio is preferably 2/1 to 1/9, more preferably 1/1 to 1/7, and further preferably 1/1 to 1/5. In addition, a preferable copolymerization ratio of the two monomers having an amide group in the copolymer of three components is preferably 1/99 to 99/1, more preferably 10/90 to 90/10, and most preferably 20/80 to 80/20, because a sufficient antifouling property and the water solubility may not be obtained when [Number of moles of monomer having an amide group]/[Number of moles of two monomers having amide groups] is too small or too large. When the copolymerization ratio of the copolymer of three components is in this range, functions such as the lubricity and the antifouling property to the lacrimal fluid are easily developed.

Another preferable aspect of the basic polymer used for the coating layer of the present invention is a copolymer of four or more components. In the case of using the copolymer of four or more components, when [Number of moles of basic monomer]/[Total number of moles of monomers other than basic monomer] is too small, the adhering property of the coating layer is deteriorated, whereas, when the ratio is too large, effects of the antifouling property and the water solubility, which are expected to the other monomers, are deteriorated, and therefore, the ratio is preferably 2/1 to 1/9, more preferably 1/1 to 1/7, and further preferably 1/1 to 1/5. A preferable copolymerization ratio when the monomers other than the basic monomer in the multi-component copolymer of four components or more are divided into water soluble monomers and water insoluble monomers is preferably 0/1 to 1/5, more preferably 0/1 to 1/4, and most preferably 5/1 to 1/3 because water solubility of the multi-component copolymer is deteriorated when [Total number of moles of water insoluble monomers]/[Total number of moles of water soluble monomers] is too large. When the copolymerization ratio of four or more monomers is in this range, functions such as the lubricity and the antifouling property to the lacrimal fluid are easily developed.

As a method for producing the acidic polymer and the basic polymer being the coating layer of the medical device, the known methods can be used. For example, in the predetermined ratio described above, monomers are formulated in a solvent and a polymerization initiator is added, and thereafter, a polymerization reaction is carried out at a predetermined temperature under presence of an inert medium with refluxing. The reacted substance obtained by the reaction is immersed into a solvent to remove non-reacted monomer components, and thereafter, the substance is washed and dried to obtain a polymer. By this method, a homopolymer or a copolymer of two components or three or more components can be produced.

In order to change various properties, for example the thickness, of the coating layer, molecular weights of the acidic polymer and the basic polymer can be changed. Specifically, when the molecular weight increases, the thickness of the coating layer generally increases. When the molecular weight is too large, however, handling may become difficult due to increase in viscosity. Therefore, each of the acidic polymer and the basic polymer used in the present invention preferably has a molecular weight of 2000 to 2000000. Each of the molecular weight is more preferably 5000 to 1000000 and further preferably 7500 to 700000. The molecular weight of the acidic polymer and the basic polymer is a mass average molecular weight in terms of polyethylene glycol measured with a gel permeation chromatography method (water-based solvent).

Application of the coating layer can be achieved by many methods as described in, for example, WO 99/35520, WO 01/57118, the disclosure of which is incorporated herein by reference, and U.S. Pat. No. 2001-0045676, the disclosure of which is incorporated herein by reference.

In the medical device of an embodiment of the present invention, a layer made of the acidic polymer and a layer made of the basic polymer (hereinafter referred to as a coating layer) is formed on at least a part of the base material surface, and at least a part of the layer may be crosslinked. In the medical device of the present invention, at least a part between the above base material and the above layer may be crosslinked. Here, the crosslink means that polymers form a crosslinking structure using their own functional groups or a crosslinking agent to bond each other.

The above crosslink can be generated by irradiating with radiation rays in a state that at least the acidic polymer and the basic polymer adhere to the base material. The radiation rays preferably include various ion beams, electron beams, positron beams, X rays, γ rays, and neutron beams, and more preferably electron beams and γ rays. The most preferable is γ rays.

By generating crosslink in the coating layer or between the coating layer and the base material as described above, excellent wettability and lubricity can be provided on a surface of a lens, and therefore, excellent wearing feeling can be provided. On the other hand, the crosslink may also be generated inside of the base material by irradiating with radiation rays, and therefore, the medical device may become too stiff. In this case, for a low water content base material, excess crosslink of inside of the base material can be reduced by carrying out copolymerization in a manner that the component A in the base material is adequately replaced to the component M. For a water-containing base material, excess crosslink of inside of the base material can be reduced by carrying out copolymerization in a manner that the cross-linkable component I in the base material is adequately replaced to the component S or the hydrophilic component H.

Subsequently, a method for producing the medical device of the present invention will be described. The medical device of the present invention is obtained by applying one or more kinds of the acidic polymer solutions and one or more kinds of the basic polymer solutions each preferably one to five times, more preferably one to three times, and further preferably one to two times to a surface of a lens-shaped or sheet-like molding (a base material) to form a coating layer. The number of times of application processes of the acidic polymer solution and the number of times of application processes of the basic polymer solution may be different.

The inventors of the present invention have found that excellent wettability and lubricity can be provided in a very small number of times of application processes of one or more kinds of the acidic polymer solutions and application processes of one or more kinds of the basic polymer solutions, which is two or three times in total. From the viewpoint of shortening in production processes, this has significantly important meaning in industry.

The inventors of the present invention is ascertained at the same time that, in the medical device of the present invention, only either the application process of the acidic polymer solution or the application process of the basic polymer solution is carried out one time, development of wettability and lubricity is hardly observed.

In the medical device of the present invention, from the viewpoint of the wettability, the lubricity, the antifouling property, and the shortening in production process, application of the coating layer is preferably carried out in constitutions selected from the following constitution 1 to 4. In the following description, each application step to a surface of a molding is sequentially carried out from the left side.

Constitution 1: Application of basic polymer solution/application of acidic polymer solution Constitution 2: Application of acidic polymer solution/application of basic polymer solution Constitution 3: Application of basic polymer solution/application of acidic polymer solution/application of basic polymer solution Constitution 4: Application of acidic polymer solution/application of basic polymer solution/application of acidic polymer solution Among these constitutions, the constitution 1 and the constitution 4 are preferable and the constitution 4 is more preferable because the obtained medical device exhibits particularly excellent wettability and antifouling property.

In the coating layer of the medical device of the present invention, in the above constitution 1 to constitution 4, at least a kind of the acidic polymer or the basic polymer used in each application process is preferably a multi-component copolymer of three or more components. As the multi-component copolymer of three or more components, the copolymers exemplified above can be used. Preferably, a final process solution contains the multi-component copolymer of three or more components. However, process solutions for first or second treatment may contain the multi-component copolymer of three or more components.

As the coating layer of the medical device of the present invention, in the constitution 1 to constitution 4, at least a kind of the acidic polymer and the basic polymer used in each application process is preferably a polymer having a group selected from a hydroxy group and an amide group, and two or more of the acidic polymer and the basic polymer are polymers having groups selected from a hydroxy group and an amide group.

As the coating layer of the medical device of the present invention, in the constitution 1 to constitution 4, at least a kind of the acidic polymer and the basic polymer used in each application process is a multi-component copolymer of three or more components and the multi-component copolymer of three or more components is preferably a polymer having a group selected from a hydroxy group and an amide group. In addition, two or more of polymers among the acidic polymer and the basic polymer are multi-component copolymers of three or more components and the multi-component copolymers of three or more components are preferably polymers having groups selected from a hydroxy group and an amide group.

As the coating layer of the medical device of the present invention, in the constitution 1 to constitution 4, at least a kind of the acidic polymer and the basic polymer used in each application process is preferably a polymer having a hydroxy group.

As the coating layer of the medical device of the present invention, in the constitution 1 to constitution 4, at least a kind of the acidic polymer and the basic polymer used in each application process is preferably a multi-component copolymer of three or more components containing one or more kinds of each of the monomer having a hydroxy group and the monomer having an amide group.

In the above production method, any one kind of the acidic polymer and the basic polymer used in the above step 2 or 3 is preferably a multi-component copolymer of three or more components.

In the coating layer of the medical device of the present invention, in the constitution 1 to the constitution 4, one or more kinds of the basic polymer solutions and/or one or more kinds of the acidic polymer solutions can be used. For example, the acidic polymer solution that is used for first and third treatment in the constitution 4 may be the same kind and the same concentration (or different concentrations) of the acidic polymer solution or different kinds of the acidic polymer solutions may be used.

When the acidic polymer solution and the basic polymer solution are applied, the surface of the base material may be an untreated or a treated surface. Here, that the surface of the base material is a treated surface means that surface treatment or surface modification is carried out to the surface of the base material by known methods. Preferable examples of the surface treatment or the surface modification include plasma treatment, chemical modification, chemical functionalization, and plasma coating.

One of the preferable aspects of the production method (aspect P1) of the medical device of the present invention is a method including the following step 1 to step 3 in this order:
<Step 1>
polymerizing a mixture including a monomer having a siloxanyl group to obtain a molding;
<Step 2>
contacting the molding to a basic polymer solution, and thereafter, washing and removing the excessive basic polymer solution; and
<Step 3>
contacting the molding to an acidic polymer solution, and thereafter, washing and removing the excessive acidic polymer solution.

In the production method described above, any one kind of the acidic polymer and the basic polymer used in the step 2 or 3 is preferably a multi-component copolymer of three or more components.

One of the preferable aspects (Aspect P2) of the production method of the medical device of the present invention is a method including the following step 1 to step 4 in this order:
<Step 1>
polymerizing a mixture including a monomer having a siloxanyl group to obtain a molding;
<Step 2>
contacting the molding to an acidic polymer solution, and thereafter, washing and removing the excessive acidic polymer solution;
<Step 3>
contacting the molding to a basic polymer solution, and thereafter, washing and removing the excessive basic polymer solution; and
<Step 4>
contacting the molding to an acidic polymer solution being the same as or different from the acidic polymer in step 2, and thereafter, washing and removing the excessive acidic polymer solution.

In the above production method, any one kind of the acidic polymer and the basic polymer used in the above steps 2 to 4 is preferably a multi-component copolymer of three or more components.

In addition, one of the preferable aspects (Aspect P3) of the production method of the medical device of the present invention is a method including the following step 1 to step 4 in this order:

<Step 1> polymerizing a mixture including a monomer having a siloxanyl group to obtain a molding;

<Step 2> contacting the molding to an acidic polymer solution, and thereafter, washing and removing the excessive acidic polymer solution;

<Step 3> contacting the molding to a basic polymer solution, and thereafter, washing and removing the excessive basic polymer solution; and <Step 4> contacting the molding to an acidic polymer solution made of a multi-component copolymer of three or more components, and thereafter, washing and removing the excessive acidic polymer solution.

The step 1 in the aspect P1 to the aspect P3 is preferably "a step for is copolymerizing a mixture including a component A that has a plurality of polymerizable functional groups in one molecule and is a polysiloxane compound having a number average molecular weight of 6000 or more and a component B that is a polymerizable monomer having a fluoroalkyl group to obtain a molding".

In addition, the step 1 in the aspect P1 to the aspect P3 is preferably "a step for copolymerizing a mixture including a component S being a monomer having a polymerizable functional group and a siloxanyl group per molecule to obtain a molding made of a silicone hydrogel containing 5% by mass or more of silicon atoms".

As described above, by sequentially contacting the molding to the acidic polymer solution and the basic polymer solution, a layer made of the acidic polymer and the basic polymer can be formed on the molding. Thereafter, preferably, the excessive polymer is sufficiently washed and removed.

As a method for contacting the molding to the acidic polymer solution or the basic polymer solution, various coating methods such as an immersion method (a dipping method), a brush coating method, a spray coating method, a spin coat method, a die coat method, and a squeegee method can be applied.

When the contact to the solution is carried out by the immersion method, an immersion time can be changed depending on many factors. Immersion of the molding to the acidic polymer solution or the basic polymer solution is carried out for preferably 1 to 30 minutes, more preferably 2 to 20 minutes, and most preferably 1 to 5 minutes.

A concentration of the acidic polymer solution and the basic polymer solution can be changed depending on properties of the acidic polymer solution and the basic polymer solution, desired thicknesses of the coating layer, and other many factors. A concentration of the acidic polymer and the basic polymer is preferably 0.001 to 10% by mass, more preferably 0.005 to 5% by mass, and most preferably 0.01 to 3% by mass.

As pH of the acidic polymer solution and the basic polymer solution, it is preferable that the pH is maintained preferably 2 to 6, more preferably 2 to 5, and further preferably 2.5 to 4.5 in the case of the acidic polymer solution whereas it is preferable that the pH is maintained preferably 8 to 12, more preferably 9 to 12, further preferably 9.5 to 11.5 in the case of the basic polymer solution.

Washing and removal of the excessive acidic polymer and basic polymer is carried out by rinsing the molding after coating generally using clean water or an organic solvent. The rinse is preferably carried out by immersing the molding to water or an organic solvent or exposing the molding to water flow or organic solvent flow. Although the rinse may be completed in one process, it has been found that carrying out a plurality of rinse processes is more effective. The rinse is preferably carried out in 2 to 5 processes. Each molding is preferably immersed to a rinsing solution for 1 to 3 minutes.

Although pure water is preferable for the rinsing solution, a buffered aqueous solution having a pH of preferably 2 to 7, more preferably 2 to 5, and further preferably 2.5 to 4.5 is preferably used in order to improve adhesion of the coating layer.

A process for drying or removing an excessive rinsing solution may be included. The molding can be dried to some extent by simply leaving to stand the molding under atmosphere. The drying, however, is preferably accelerated by blowing moderate air flow to the surface. A flow rate of the air flow can be adjusted as a function of strength of a material to be dried and fixturing of the material. The molding does not need to be fully dried. Here, removal of droplets of the solution adhering to the molding surface is rather important than the drying of the molding. Therefore, the drying may be carried out to the extent that only a film of water or the solution on the molding surface is removed, and this is preferable because of reduction in process time.

As described in the constitution 1 to the constitution 4, the acidic polymer and the basic polymer are preferable alternately applied on the molding. By alternately applying, the medical device having excellent wettability and lubricity, which cannot be obtained by either of the application processes alone, and further excellent wearing feeling can be obtained.

In the medical device of the present invention, the coating layer may be asymmetry. Here, the "asymmetry" means that the medical device has different coating layers on a first surface and an opposite second surface. Here, the "different coating layers" mean that the coating layer formed in the first surface and the coating layer formed on the second surface have different surface characteristics or functionalities.

The thickness of the coating layer can be adjusted by adding one or more salt such as sodium chloride to the acidic polymer solution or the basic polymer solution. A preferable concentration of the salt is 0.1 to 2.0% by mass. As the concentration of the salt is increased, a polymer electrolyte forms a more spherical space structure. When the concentration is too high, however, the polymer electrolyte does not deposit well on the molding surface, even if the polymer electrolyte deposits. A more preferable concentration of the salt is 0.7 to 1.3% by mass.

One of the other preferable aspects of the production method of the medical device of the present invention is a method further including the following step 5:

<Step 5> forming the layer made of the acidic polymer and the basic polymer on the molding by the previous step, and thereafter irradiating the molding with radiation rays.

The irradiation of the radiation rays may be carried out in a state of immersing the molding into the coating liquid or may be carried out after the molding is pulled out from the coating liquid and washed. In addition, the irradiation of the radiation rays is preferably carried out in the state of immersing the molding in a liquid other than the coating liquid. This case is preferable because the radiation rays more effectively affect. In this case, as a solvent for the liquid used for immersing the coated molding, various types of organic and inorganic solvents are applicable and are not particularly limited. By way of example, water; various alcohol-based solvents such as methanol, ethanol, propanol, 2-propanol, butanol, tert-butanol, tert-amyl alcohol, and 3,7-dimethyl-3-octanol; various aromatic hydrocarbon solvents such as benzene, toluene, and xylene; various aliphatic hydrocarbon solvents such as hexane, heptane, octane, decane, petroleum ether, kerosene, ligroin and paraffin; various ketone-based solvents such as acetone, methylethyl ketone, and methylisobutyl ketone; various ester-based solvents such as ethyl acetate, butyl acetate, methyl benzoate, dioctyl phthalate, and ethylene glycol diacetate; diethyl ether, tetrahydrofuran, dioxane, and various glycol ether-based solvents such as ethylene glycol dialkyl ether, diethylene glycol dialkyl ethers, triethylene glycol dialkyl ether, tetraethylene glycol dialkyl ethers, polyethylene glycol dialkyl ethers, a polyethylene glycol-polypropylene glycol block copolymer, and a polyethylene glycol- and polypropylene glycol random copolymer are included, and these solvents can be used singly or by mixing. Among them, the most preferable is water. When the molding in a state of being immersed in a water-based liquid is irradiated with the radiation rays, physiologic saline, phosphoric acid-based buffer solution (preferably a pH of 7.1 to 7.3), and boric acid-based buffer solution (preferably a pH of 7.1 to 7.3), other than pure water are preferable as water-based liquids.

If the molding is irradiated with the radiation rays in a state of being enclosed in a sealed container, there is an advantage that the molding is simultaneously sterilized.

As the radiation ray, γ ray is preferably used. In this case, when a radiation dose of irradiated γ ray is too small, sufficient bonding between the molding and the coating layer is not obtained, whereas, when the radiation dose is too large, physical properties of the molding is deteriorated, and therefore, the radiation dose is preferably 0.1 to 100 kGy, more preferably 15 to 50 kGy, and most preferably 20 to 40 kGy. By this irradiation, at least a part of inside of the coating layer and at least a part between the coating layer and the molding are crosslinked, and therefore, durability of the coating layer (for example, durability for washing by rubbing) can be improved.

The medical device of the present invention is useful for soft ophthalmic lenses, particularly, ophthalmic lenses such as a soft contact lens, an intraocular lens, an artificial cornea, a corneal inlay, a corneal onlay, and spectacle lenses. Among them, medical device is particularly preferable for the soft contact lens.

EXAMPLES

Hereinafter, the present invention will be specifically described with reference to Examples. The present invention, however, is not limited to Examples.

(Analysis Method and Evaluation Method)

In this specification, a wet state means a state in which a sample is immersed in pure water or a borate buffer solution at room temperature (25° C.) for 24 hours or more. After the sample is taken out from pure water or the borate buffer solution, the measurement of physical properties in the wet state is carried out as soon as possible.

In this specification, a dry state means a state in which a wet state sample is dried under vacuum at 40° C. for 16 hours. A degree of vacuum in the vacuum drying is set to 2 hPa or less. After the vacuum drying, measurement of physical properties in the dry state is carried out as soon as possible.

In this specification, a borate buffer solution is a "salt solution" described in Example 1 of Japanese Translation of PCT Application No. 2004-517163, the disclosure of which is incorporated herein by reference. Specifically, the borate buffer solution is made by dissolving 8.48 g of sodium chloride, 9.26 g of boric acid, 1.0 g of sodium borate (sodium tetraborate decahydrate), and 0.10 g ethylenediamine tetraacetic acid into pure water to prepare 1000 mL of an aqueous solution.

(1) Molecular Weight

If not otherwise specified, a mass average molecular weight and a number average molecular weight are measured by a GPC method under the following conditions.

Pump: DP-8020 manufactured by TOSOH CORPORATION

Detector: RI-8010 manufactured by TOSOH CORPORATION

Column oven: CTO-6A manufactured by Shimadzu Corporation

Autosampler: AS-8010 manufactured by TOSOH CORPORATION

Column: TSKgel GMHHR-M (inner diameter 7.8 mm×30 cm, particle size 5 μm)×2, manufactured by TOSOH CORPORATION Column temperature: 35° C.

Mobile phase: Chloroform

Flow rate: 1.0 mL/min

Sample concentration: 0.4% by mass

Injection volume: 100 μL

Standard sample: Polystyrene (molecular weight 1010 to 1090000)

(2) Wettability

A contact lens-shaped test specimen was immersed in the borate buffer solution in a beaker at room temperature for 24 hours or more. The beaker containing the borate buffer solution and the test specimen was subjected to an ultrasonic cleaner (1 minute). The test specimen was pulled out from the borate buffer solution and surface appearance at the time of holding the test specimen in the air so as to set a diameter direction perpendicular was visually observed, and the surface appearance was determined according to the following criteria. Here, the diameter is a diameter of a circle formed by the edge of the contact lens.

A: A liquid film on the surface was retained for more than 20 seconds.

B: A liquid film on the surface was broken from 10 seconds or more to less than 20 seconds.

C: A liquid film on the surface was broken from 5 seconds or more to less than 10 seconds.

D: A liquid film on the surface was broken from 1 second or more to less than 5 seconds.

E: A liquid film on the surface was broken in a moment (less than 1 second).

(3) Lubricity

The lubricity was measured by a sensitive evaluation when a sample (in a contact lens shape) in the wet state with the borate buffer solution was rubbed five times with human fingers.

A: The sample had extremely excellent lubricity.

B: The sample had lubricity about in the middle of A and B.

C: The sample had medium lubricity.

D: The sample had almost no lubricity (about in the middle of C and E).

E: The sample had no lubricity.

(4) Mucin Adhesion

As the mucin, Mucin, Bovine Submaxillary Gland manufactured by CALBIOCHEM CORPORATION (Catalog No. 499643) was used. The contact lens-shaped sample was immersed in a mucin aqueous solution having a concentration of 0.1% by mass under conditions of 37° C. for 20 hours, and thereafter, an amount of mucin adhering to the sample was quantitatively determined by a BCA (bicinchoninic acid) protein assay method.

(5) Lipid Adhesion

A stirring bar (36 mm) was placed into a 500 ml of beaker, and then 1.5 g of methyl palmitate and 500 g of pure water were charged. A temperature of a water bath was set to 37° C.; the above beaker was placed at the center of the water bath; and the mixture was stirred with a magnetic stirrer for 1 hour. A rotation speed was set to 600 rpm. The contact lens-shaped samples were placed one by one in a lens basket and the basket was placed in the above beaker to stir without modification. One hour later, stirring was stopped and the samples in the lens basket were washed by rubbing with water of 40° C. and a liquid household detergent ("Mamalemon (registered trademark)", manufactured by Lion Corporation). The samples after washing were placed into a screw tube containing the borate buffer solution (pH 7.1 to 7.3) and the screw tube was immersed into an ice bath for 1 hour. After the screw tube was taken out from the ice bath, white turbidity of the sample was visually observed and an adhesion amount of methyl palmitate to the sample was determined by the following criteria.

A: The sample had no white turbidity and was clear.
B: The sample had white turbidity in few parts.
C: The sample had white turbidity in many parts.
D: The sample had white turbidity in almost all parts.
E: The sample entirely had white turbidity.

(6) Immersion Test into Artificial Lacrimal Fluid

As an artificial lacrimal fluid, a tear-like fluid (TLF) buffer solution was prepared according to a method described in WO 2008/127299, the disclosure of which is incorporated herein by reference, page 32, lines 5 to 36, except that oleic acid was used instead of oleic acid propyl ester. In one well in a multi-plate for culture (24-well type, material polystyrene, radiation sterilized), 2 ml of the artificial lacrimal fluid is poured and a piece of sample (a contact lens shape) was immersed. The multi-plate was shaken at 100 rpm at 37° C. for 24 hours. Thereafter, the sample was taken out, and after the sample was lightly washed with a phosphate buffer solution (PBS), the sample was immersed into the well in which 2 ml of the lacrimal fluid was replaced. After the multi-plate was further shaken at 100 rpm at 37° C. for 24 hours, the sample was lightly washed with PBS and an amount of adhering substance was observed by visually evaluating a degree of white turbidity of the sample. The evaluation was carried out based on the following criteria.

A: No white turbidity was observed.
B: The sample had white turbidity in few parts (less than 10% in terms of area).
B: The sample had white turbidity in many parts (10% to 50% in terms of area).
D: The sample had white turbidity in almost all parts (50% to 100% in terms of area), but the backside was seen through the sample.
E: The sample entirely had thick white turbidity, and the backside was difficult to be seen through the sample.

(7) Dynamic Contact Angle Measurement

The dynamic contact angle was measured with a sample in the wet state with the borate buffer solution using a dynamic wettability tester WET-6000 manufactured by RHESCA Corporation Limited. As a dynamic contact angle sample, a film-shaped test specimen having a size of about 5 mm×10 mm×0.1 mm that is cut out from a sample formed in a film shape or a strip-shaped specimen having a width of 5 mm that is cut out from a contact lens-shaped sample was used to measure a dynamic contact angle to the borate buffer solution at the time of advance. An immersion rate was set to 0.1 mm/sec and an immersion depth was set to 7 mm.

(8) Water Content

A test specimen having a contact lens shape was used. After the test specimen was immersed in the borate buffer solution and left to stand at room temperature for 24 hours or more, the water adhering to the surface was wiped off with a wiping cloth ("Kimwipe (registered trademark)" manufactured by NIPPON PAPER CRECIA Co., LTD.) to measure a mass (Ww). Thereafter, the test specimen was dried with a vacuum dryer at 40° C. for 16 hours to measure a mass (Wd). The water content was calculated from the following formula. When the obtained value was less than 1%, the value was determined to be equal to or less than measurement limit and represented as "less than 1%".

$$\text{Water content (\%)} = 100 \times (Ww - Wd)/Ww$$

(9) Total Light Transmittance

The total light transmittance was measured using SM Color Computer (model SM-7-CH, manufactured by Suga Test Instruments Co., Ltd.). The water on the lens-shaped sample was lightly wiped off and the total light transmittance was measured by setting the sample in an optical path. A thickness was measured using ABC Digimatic Indicator (ID-C112, manufactured by Mitutoyo Corporation) and the sample having the thickness of 0.14 to 0.15 mm was used for measurement.

(10) Tensile Modulus and Tensile Elongation (Elongation at Break)

These properties were measured using a sample in the wet state by the borate buffer solution. A test specimen having a width (a minimum part) of 5 mm, a length of 14 mm, and a thickness of 0.2 mm was cut out from the contact lens-shaped sample using a specific cutting die. A tensile test was carried out using the test specimen with Tensilon Type RTM-100 manufactured by Orientec Co., Ltd. A tensile speed was 100 mm/minute and a distance between grips (an initial value) was 5 mm.

(11) Scrubbing Resistance

A depressed area is made in the center of a palm and a sample (a contact lens shape) in the wet state with the borate buffer solution was placed in the depressed area. A wash fluid ("Renu (registered trademark)" Bausch & Lomb Incorporated) was added to the depressed area and each of the front surface and the back surface was rubbed 10 times by the ball of the index finger of the other hand. Thereafter, the both surfaces of the sample were rubbed 20 times with the sample being clamped by the thumb and the index finger and the wash fluid being poured. The sample after washing by rubbing was immersed into the borate buffer solution. Thereafter, the lubricity (3) was evaluated.

(Preparation of Molding)

Reference Example 1

Polydimethylsiloxane Having Methacryloyl Groups at Both Ends Represented by the Following Formula (M2)

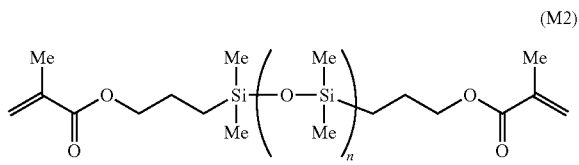

(M2)

(FM7726, Chisso Corporation, mass average molecular weight 29 kD, number average molecular weight 26 kD) (50 parts by mass) as the component A, trifluoroethyl acrylate (Viscoat 3F, Osaka Organic Chemical Industry Ltd.) (45 parts by mass) as the component B, 2-ethylhexyl acrylate (2-EHA, 3 parts by mass) as the component C, N,N-dimethylaminoethyl acrylate (DMAEA, 1 part by mass) as the component C, an ultraviolet absorber having a polymerizable group (RUVA-93, Otsuka Chemical Co., Ltd.) (1 part by mass) as the component Ck, a colorant having a polymerizable group represented by the following estimated structural formula (C3H)

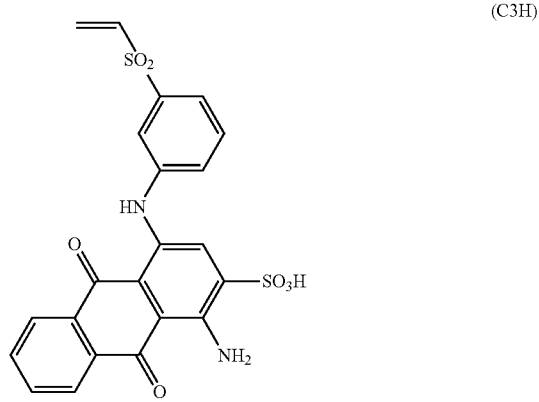

(C3H)

[a colorant made by treating Uniblue A (Sigma-Aldrich Corporation) with hydrochloric acid](0.04 parts by mass) as the component Ck, a polymerization initiator "Irgacure (registered trademark)" 819 (Ciba Specialty Chemicals Inc., 0.75 parts by mass), and t-amyl alcohol (10 parts by mass) as a solvent were mixed and stirred. Insoluble matter was removed by filtering the mixture with a membrane filter (0.45 μm) to obtain a monomer mixture. This monomer mixture was poured into a test tube and degassed under a reduced pressure of 20 Torr (27 hPa) while stirring using a touch mixer, and thereafter, the pressure was returned to atmospheric pressure with argon gas. This operation was repeated three times. In a glove box under nitrogen atmosphere, the monomer composition was filled in a cavity of a mold for a contact lens made of clear resin (poly 4-methylpentene-1) and polymerized by a light irradiation (8000 lux, 20 minutes) using fluorescent lamps (TOSHIBA CORPORATION FL-6D, daylight color, 6 W, four lamps). After the polymerization, the mold containing the molded polymer was immersed into 60% by mass isopropyl alcohol aqueous solution, and thereby, a molding having a contact lens shape was peeled off from the mold. The obtained molding was immersed into a large excess amount of 80% by mass isopropyl alcohol aqueous solution at 60° C. for 2 hours. Furthermore, the molding was immersed into a large excess amount of 50% by mass isopropyl alcohol aqueous solution at room temperature for 30 minutes, and then immersed into a large excess amount of 25% by mass isopropyl alcohol aqueous solution at room temperature for 30 minutes, and then immersed into a large excess amount of pure water at room temperature for 30 minutes. Finally, the molding was placed in a sealed vial container in a state of immersing into clean pure water, and sterilized in an autoclave at 121° C. for 30 minutes. The obtained molding had an edge part diameter of about 14 mm and a thickness at the center part of about 0.07 mm. The obtained molding had a water content of less than 1%, a tensile modulus of 0.614 MPa, and an elongation at break of 593%, was clear, and had no turbidity, and thus, was suitable for a contact lens. In addition, a similar operation was carried out using two glass plates and a gasket as a mold to obtain a film-like sample of 60 mm×60 mm×0.25 mm.

Reference Example 2

A silicone monomer (13.4 parts by mass) represented by the following formula (t3)

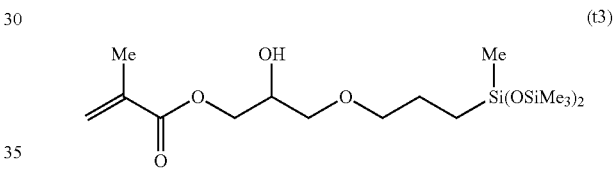

(t3)

as the component S, a silicone monomer (36.6 parts by mass) represented by the following formula (t4)

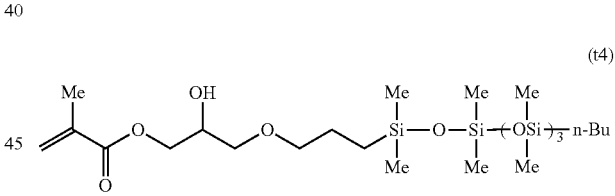

(t4)

as the component S, N,N-dimethylacrylamide (37 parts by mass) as the hydrophilic component H, 2-hydroxyethyl methacrylate (9.2 parts by mass) as the hydrophilic component H, triethylene glycol dimethacrylate (1.26 parts by mass) as the cross-linkable component I, an ultraviolet absorber having a polymerizable group (RUVA-93, Otsuka Chemical Co., Ltd.) (1.26 parts by mass) as the component Ck, a colorant having a polymerizable group [Uniblue A, Sigma-Aldrich Corporation] (0.02 parts by mass) as the component Ck, a photoinitiator Irgacure 1850 (1.26 parts by mass), and tetrahydrolinalool (23.9 parts by mass) as a solvent were mixed and stirred. A homogeneous and clear monomer composition was obtained. The monomer composition was degassed under argon atmosphere. In a glove box under nitrogen atmosphere, the monomer composition was filled in a cavity of a mold having a lens shape and a lens was obtained by light irradiation (TOSHIBA CORPORATION FLED, 8.4 kilolux, 20 minutes). After the obtained lens was immersed into 60% IPA aqueous solution at 60° C. for 30 minutes and released from the mold, impurities such as remaining monomers were extracted by immersing the lens into 80% IPA aqueous solution at 60° C. for 2 hours and the lens was hydrated by immersing each liquid of 50% IPA aqueous solution, 25% IPA aqueous solution, and water, in which IPA concentrations were decreased stepwise, for about 30 minutes. The lens was immersed into the borate buffer solution (pH 7.1 to 7.3) in a 5 mL vial container, and the vial container was placed in an autoclave to carry out boiling treatment at 120° C. for 30 minutes. The obtained lens had an edge part diameter of about 14 mm and a thickness at the center part of about 0.07 mm. The obtained lens had a silicon atom content of 12.3%, a water content of 41.7%, a tensile modulus of 0.665 MPa, and a total light transmittance of 84.2%, was clear, and had no turbidity, and thus, was suitable for a contact lens.

(Synthesis of Polymer for Coating)

Synthesis Examples of copolymers provided for coating in Examples are described, and, in Synthesis Examples, molecular weights of each copolymer were measured under conditions described below.

GPC measurement conditions of the polymer for coating are as follows.
Equipment: Prominence GPC System manufactured by Shimadzu Corporation
Pump: LC-20AD
Autosampler: SIL-20AHT
Column oven: CTO-20A
Detector: RID-10A
Column: GMPWXL (inner diameter 7.8 mm×30 cm, particle size 13 μm), manufactured by TOSOH CORPORATION
Solvent: Water/methanol=1/1 (0.1 N lithium nitrate is added)
Flow rate: 0.5 mL/min
Measurement time: 30 minutes
Sample concentration: 0.1% by mass
Injection volume: 100 μL
Standard sample: Polyethylene oxide standard sample (0.1 kD to 1258 kD) manufactured by Agilent.

Synthesis Example 1

CPHDA: 2-hydroxyethyl methacrylate/N,N-dimethylacrylamide/acrylic acid (a molar ratio of 1/2/1)

Into a 200 mL three-necked flask, 2-hydroxyethyl methacrylate (3.25 g, 0.025 mol) as the monomer having a hydroxy group, N,N-dimethylacrylamide (4.96 g, 0.050 mol) as the monomer having an amide group, acrylic acid (1.80 g, 0.025 mol) as the acidic monomer, dimethylsulfoxide (41.0 g) as a solvent, and a polymerization initiator VA-061 (Wako Pure Chemical Industries, Ltd., 0.008 g, 0.031 mmol) were added, and the three-necked flask was equipped with a three-way cock, a reflux condenser, a thermometer, and a mechanical stirrer. A monomer concentration was 20% by mass.

After inside of the three-necked flask was degassed with a vacuum pump and argon replacement was carried out for 3 times, the mixture was stirred at 60° C. for 0.5 hours, and thereafter, the temperature was raised to 70° C. and the mixture was stirred for 4.5 hours. After completion of the polymerization, the polymerization reaction liquid was cooled to room temperature and the liquid was poured to 50 mL of ethyl acetate and the obtained mixture was left to stand for one night. In the next day, a supernatant liquid was removed by decantation. The obtained solid content was washed 10 times with methanol/n-hexane=8 mL/40 mL. The solid content was dried at 60° C. for one night with a vacuum drier. After liquid nitrogen was poured to the solid content and the solid content was fragmentized with a spatula, the solid content was dried at 60° C. for 3 hours with a vacuum drier. Molecular weights of thus obtained copolymer were a Mn of 123 kD and a Mw of 428 kD (Mw/Mn=3.48).

Synthesis Example 2

CPHDA: 2-hydroxyethyl methacrylate/N,N-dimethylacrylamide/acrylic acid (a molar ratio of 1/2/1)

Into a 200 mL three-necked flask, 2-hydroxyethyl methacrylate (3.25 g, 0.025 mol) as the monomer having a hydroxy group, N,N-dimethylacrylamide (4.96 g, 0.050 mol) as the monomer having an amide group, acrylic acid (1.80 g, 0.025 mol) as the acidic monomer, dimethylsulfoxide (41.0 g) as a solvent, a polymerization initiator VA-061 (Wako Pure Chemical Industries, Ltd., 0.016 g, 0.062 mmol), and 2-mercaptoethanol (2-ME, 14 μL, 0.2 mmol) were added, and the three-necked flask was equipped with a three-way cock, a reflux condenser, a thermometer, and a mechanical stirrer. A monomer concentration was 20% by mass. After inside of the three-necked flask was degassed with a vacuum pump and argon replacement was carried out for 3 times, the mixture was stirred at 60° C. for 0.5 hours, and thereafter, the temperature was raised to 70° C. and the mixture was stirred for 4.5 hours. After completion of the polymerization, the polymerization reaction liquid was cooled to room temperature and the liquid was poured to 50 mL of ethyl acetate and the obtained mixture was left to stand for one night. In the next day, a supernatant liquid was removed by decantation. The obtained solid content was washed 10 times with methanol/n-hexane=8 mL/40 mL. The solid content was dried at 60° C. for one night with a vacuum drier. After liquid nitrogen was poured to the solid content and the solid content was fragmentized with a spatula, the solid content was dried at 60° C. for 3 hours with a vacuum drier. Molecular weights of thus obtained copolymer were a Mn of 49 kD and a Mw of 103 kD (Mw/Mn=2.11).

Synthesis Example 3

CPHDA: 2-hydroxyethyl methacrylate/N,N-dimethylacrylamide/acrylic acid (a molar ratio of 1/2/1)

Into a 200 mL three-necked flask, 2-hydroxyethyl methacrylate (3.25 g, 0.025 mol) as the monomer having a hydroxy group, N,N-dimethylacrylamide (4.96 g, 0.050 mol) as the monomer having an amide group, acrylic acid (1.80 g, 0.025 mol) as the acidic monomer, dimethylsulfoxide (41.0 g) as a solvent, a polymerization initiator VA-061 (Wako Pure Chemical Industries, Ltd., 0.016 g, 0.062 mmol), and 2-mercaptoethanol (2-ME, 43 μL, 0.62 mmol) were added, and the three-necked flask was equipped with a three-way cock, a reflux condenser, a thermometer, and a mechanical stirrer. A monomer concentration was 20% by mass. After inside of the three-necked flask was degassed with a vacuum pump and argon replacement was carried out for 3 times, the mixture was stirred at 60° C. for 0.5 hours, and thereafter, the temperature was raised to 70° C. and the mixture was stirred for 4.5 hours. After completion of the polymerization, the polymerization reaction liquid was cooled to room temperature and the liquid was poured to 500 mL of ethyl acetate and the obtained mixture was left to stand for one night. In the next day, a supernatant liquid was removed by decantation. The obtained solid content was washed 10 times with methanol/ n-hexane=5 mL/50 mL. The solid content was dried at 60° C. for one night with a vacuum drier. After liquid nitrogen was poured to the solid content and the solid content was fragmentized with a spatula, the solid content was dried at 60° C. for 3 hours with a vacuum drier. Molecular weights of thus obtained copolymer were a Mn of 22 kD and a Mw of 42 kD (Mw/Mn=1.89).

Synthesis Example 4

CPHDA: 2-hydroxyethyl methacrylate/N,N-dimethylacrylamide/acrylic acid (a molar ratio of 2/1/1)

Into a 200 mL three-necked flask, 2-hydroxyethyl methacrylate (6.51 g, 0.050 mol) as the monomer having a hydroxy group, N,N-dimethylacrylamide (2.48 g, 0.025 mol) as the monomer having an amide group, acrylic acid (1.80 g, 0.025 mol) as the acidic monomer, dimethylsulfoxide (43.2 g) as a solvent, a polymerization initiator VA-061 (Wako Pure Chemical Industries, Ltd., 0.016 g, 0.062 mmol), and 2-mercaptoethanol (2-ME, 43 μL, 0.62 mmol) were added, and the three-necked flask was equipped with a three-way cock, a reflux condenser, a thermometer, and a mechanical stirrer. A monomer concentration was 20% by mass. After inside of the three-necked flask was degassed with a vacuum pump and argon replacement was carried out for 3 times, the mixture was stirred at 60° C. for 0.5 hours, and thereafter, the temperature was raised to 70° C. and the mixture was stirred for 4.5 hours. After completion of the polymerization, the polymerization reaction liquid was cooled to room temperature and the liquid was poured to 500 mL of ethyl acetate and the obtained mixture was left to stand for one night. In the next day, a supernatant liquid was removed by decantation. The obtained solid content was washed 10 times with methanol/n-hexane=5 mL/50 mL. The solid content was dried at 60° C. for one night with a vacuum drier. After liquid nitrogen was poured to the solid content and the solid content was fragmentized with a spatula, the solid content was dried at 60° C. for 3 hours with a vacuum drier. Molecular weights of thus obtained copolymer were a Mn of 17 kD and a Mw of 33 kD (Mw/Mn=1.98).

Synthesis Example 5

CPHDA: 2-hydroxyethyl methacrylate/N,N-dimethylacrylamide/acrylic acid (a molar ratio of 1.5/1.5/1)

Into a 200 mL three-necked flask, 2-hydroxyethyl methacrylate (4.88 g, 0.038 mol) as the monomer having a hydroxy group, N,N-dimethylacrylamide (3.72 g, 0.038 mol) as the monomer having an amide group, acrylic acid (1.80 g, 0.025 mol) as the acidic monomer, dimethylsulfoxide (41.6 g) as a solvent, a polymerization initiator VA-061 (Wako Pure Chemical Industries, Ltd., 0.016 g, 0.062 mmol) were added, and the three-necked flask was equipped with a three-way cock, a reflux condenser, a thermometer, and a mechanical stirrer. A monomer concentration was 20% by mass. After inside of the three-necked flask was degassed with a vacuum pump and argon replacement was carried out for 3 times, the mixture was stirred at 60° C. for 0.5 hours, and thereafter, the temperature was raised to 70° C. and the mixture was stirred for 4.5 hours. After completion of the polymerization, the polymerization reaction liquid was cooled to room temperature and the liquid was poured to 50 mL of ethyl acetate and the obtained mixture was left to stand for one night. In the next day, a supernatant liquid was removed by decantation. The obtained solid content was washed 10 times with methanol/n-hexane=8 mL/40 mL. The solid content was dried at 60° C. for one night with a vacuum drier. After liquid nitrogen was poured to the solid content and the solid content was fragmentized with a spatula, the solid content was dried at 60° C. for 3 hours with a vacuum drier. Molecular weights of thus obtained copolymer were a Mn of 83 kD and a Mw of 319 kD (Mw/Mn=3.85).

Synthesis Example 6

CPDA: N,N-dimethylacrylamide/acrylic acid (a molar ratio of 2/1)

Into a 500 mL three-necked flask, N,N-dimethylacrylamide (59.50 g, 0.600 mol) as the monomer having an amide group, acrylic acid (21.62 g, 0.300 mol) as the acidic monomer, pure water (325.20 g), a polymerization initiator VA-061 (Wako Pure Chemical Industries, Ltd., 0.1408 g, 0.562 mmol), and 2-mercaptoethanol (43.8 μL, 0.63 mmol) were added, and the three-necked flask was equipped with a three-way cock, a reflux condenser, a thermometer, and a mechanical stirrer. A monomer concentration was 20% by mass. After inside of the three-necked flask was degassed with a vacuum pump and argon replacement was repeated for 3 times, the mixture was stirred at 50° C. for 0.5 hours, and thereafter, the temperature was raised to 70° C. and the mixture was stirred for 6.5 hours. After completion of the polymerization, the polymerization reaction solution was concentrated to 400 g with an evaporator and the mixture was poured into 2-propanol/n-hexane=500 mL/500 mL and was left to stand, and thereafter, supernatant liquid was removed by decantation. An obtained solid content was washed three times with 2-propanol/n-hexane=250 mL/250 mL. The solid content was dried at 60° C. for one night with a vacuum drier. After liquid nitrogen was poured to the solid content and the solid content was fragmentized with a spatula, the solid content was dried at 60° C. for 3 hours with a vacuum drier. A molecular weight of thus obtained copolymer was an Mn of 55 kD and an Mw of 192 kD (Mw/Mn=3.5).

(Preparation of Coating Solution)

Hereinafter, pure water represents water purified by filtering with a reverse osmosis membrane.

<PEI Solution>

Polyethyleneimine (P3143, Sigma-Aldrich Corporation, a molecular weight of 750000) was dissolved into pure water to prepare 1% by mass aqueous solution.

<PAA Solution>

Polyacrylic acid (169-18591, Wako Pure Chemical Industries, Ltd., a molecular weight of 250000) was dissolved into pure water to prepare 1.2% by mass aqueous solution.

<Solution of Copolymer>

Each of the copolymers obtained in Synthesis Examples listed in Table 1 was dissolved in a solvent listed in Table 1 to prepare CPHDA solutions A to E and a CPDA solution having concentrations listed in Table 1.

TABLE 1

| | Copolymer | Monomer having hydroxy group (A) | Monomer having amide group (B) | Acidic monomer (C) | A (Molar ratio) | B (Molar ratio) | C (Molar ratio) | Mn (kD) | Mw (kD) | Solvent | Solution concentration (% by mass) |
|---|---|---|---|---|---|---|---|---|---|---|---|
| CPHDA solution A | Synthesis Example 1 | HEMA | DMA | AA | 1 | 2 | 1 | 123 | 428 | Pure water | 1 |
| CPHDA solution B | Synthesis Example 2 | HEMA | DMA | AA | 1 | 2 | 1 | 49 | 103 | Pure water | 1 |
| CPHDA solution C | Synthesis Example 3 | HEMA | DMA | AA | 1 | 2 | 1 | 22 | 42 | Pure water | 1 |
| CPHDA solution D | Synthesis Example 4 | HEMA | DMA | AA | 2 | 1 | 1 | 17 | 33 | Pure water | 1 |
| CPHDA solution E | Synthesis Example 5 | HEMA | DMA | AA | 1.5 | 1.5 | 1 | 83 | 319 | Pure water | 1 |
| CPDA solution | Synthesis Example 6 | — | DMA | AA | — | 2 | 1 | 55 | 192 | Pure water | 1 |

DMA: N,N-dimethylacrylamide
HEMA: 2-hydroxyethyl methacrylate
AA: Acrylic acid

Examples 1 to 10

A layer made of an acidic polymer and a basic polymer (a coating layer) was formed on the moldings obtained in Reference Examples 1 and 2. Each of the moldings listed in Table 2 was immersed into a first solution listed in Table 2 for 30 minutes, and thereafter, immersed into three pure water baths for 5 minutes each. Subsequently, the molding was immersed into a second solution listed in Table 2 for 30 minutes, and thereafter, immersed into three pure water baths for 5 minutes each. Subsequently, the molding was immersed into a third solution listed in Table 2 for 30 minutes, and thereafter, immersed into three pure water baths for 5 minutes each. With respect to each of the samples on which the coating layer was formed, evaluation such as the mucin adhesion and the lubricity was carried out. The evaluation results are listed in Table 2.

Comparative Examples 1 to 6

The molding obtained in each Reference Example listed in Table 2 was immersed into the first solution listed in Table 2 for 30 minutes, and thereafter, immersed into three pure water baths for 5 minutes each. Subsequently, the molding was immersed into the second solution listed in Table 2 for 30 minutes, and thereafter, immersed into three pure water baths for 5 minutes each. Subsequently, the molding was immersed into the third solution listed in Table 2 for 30 minutes, and thereafter, immersed into three pure water baths for 5 minutes each. The obtained evaluation results are listed in Table 2. In Table 2, "–" means that treatment by each polymer solution was not carried out (Comparative Example 1 is a base material to which treatment with the first to the third solutions were not carried out, that is, on which the coating layer was not formed).

TABLE 2

| | Molding used for coating | First solution | Second solution | Third solution | Mucin adhesion (μg/cm²) | Slipperiness | Wettability | Dynamic contact angle (advance) | Immersion test into artificial lacrimal fluid | Lipid adhesion | Durability to washing by rubbing |
|---|---|---|---|---|---|---|---|---|---|---|---|
| Example 1 | Reference Example 1 | PAA solution | PEI solution | CPHDA solution A | 1.95 | A | B | 69 | D | C | C |
| Example 2 | Reference Example 1 | PAA solution | PEI solution | CPHDA solution B | 1.87 | A | B | 60 | C | B | C |
| Example 3 | Reference Example 1 | PAA solution | PEI solution | CPHDA solution C | 1.97 | A | B | 88 | C | C | C |
| Example 4 | Reference Example 1 | PAA solution | PEI solution | CPHDA solution D | 1.81 | A | B | 73 | D | C | C |
| Example 5 | Reference Example 1 | PAA solution | PEI solution | CPHDA solution E | 1.92 | A | B | 58 | C | C | C |
| Example 6 | Reference Example 2 | PAA solution | PEI solution | CPHDA solution A | 10.79 | A | C | 78 | E | A | C |
| Example 7 | Reference Example 2 | PAA solution | PEI solution | CPHDA solution B | 6.82 | A | C | 61 | E | A | C |
| Example 8 | Reference Example 2 | PAA solution | PEI solution | CPHDA solution C | 20.79 | C | C | 90 | E | A | C |
| Example 9 | Reference Example 2 | PAA solution | PEI solution | CPHDA solution D | 7.58 | A | C | 68 | E | A | C |
| Example 10 | Reference Example 2 | PAA solution | PEI solution | CPHDA solution E | 8.95 | C | C | 60 | E | A | C |
| Comparative Example 1 | Reference Example 1 | — | — | — | 1.51 | E | E | 118 | E | C | E |
| Comparative Example 2 | Reference Example 1 | PAA solution | PEI solution | PAA solution | 2.89 | A | A | 36 | E | D | C |
| Comparative Example 3 | Reference Example 1 | PAA solution | PEI solution | CPDA solution | 2.53 | A | A | 76 | E | D | C |

TABLE 2-continued

| | Molding used for coating | First solution | Second solution | Third solution | Mucin adhesion (μg/cm²) | Slipperiness | Wettability | Dynamic contact angle (advance) | Immersion test into artificial lacrimal fluid | Lipid adhesion | Durability to washing by rubbing |
|---|---|---|---|---|---|---|---|---|---|---|---|
| Comparative Example 4 | Reference Example 2 | — | — | — | 3.86 | E | E | 106 | D | E | E |
| Comparative Example 5 | Reference Example 2 | PAA solution | — | — | 11.08 | A | A | 34 | E | D | C |
| Comparative Example 6 | Reference Example 2 | PAA solution | PEI solution | PAA solution | 5.14 | B | B | 72 | E | B | C |

In the case of the low water content base materials prepared in Reference Example 1 (Examples 1 to 5), medical devices having excellent wettability and lubricity, and reducing the mucin adhesion, the artificial lacrimal fluid adhesion, and the lipid adhesion were obtained. When the water-containing base materials in Reference Example 2 were used (Examples 6 to 10), medical devices having adequate wettability and lubricity, and excellent lipid adhesion resistance were obtained.

Comparative Example 7

After the lens obtained in Reference Example 1 was immersed into 1% by mass PVP K90 aqueous solution (polyvinylpyrrolidone, Sigma-Aldrich Japan K. K., a molecular weight of 360000) at room temperature for 30 minutes, the lens was taken out and touched with a human finger, and as a result, the lens has very excellent lubricity. This lubricity is A in the evaluation criteria of lubricity. Thereafter, the lens is lightly rinsed with pure water in a beaker, and touched with the human finger, and as a result, the lens has no lubricity. This lubricity is E in the evaluation criteria of lubricity.

Comparative Example 8

After the lens obtained in Reference Example 2 was immersed into 1% by mass PVP K90 aqueous solution (polyvinylpyrrolidone, Sigma-Aldrich Japan K. K., a molecular weight of 360000) at room temperature for 30 minutes, the lens was taken out and touched with human fingers, and as a result, the lens has very excellent lubricity. This lubricity was A in the evaluation criteria of lubricity. Thereafter, the lens was lightly rinsed with pure water in a beaker, and touched with human fingers, and as a result, the lens has no lubricity. This lubricity was E in the evaluation criteria of lubricity.

The present invention relates to the medical device, and is suitably employed for a device, for example, an ophthalmic lens or a material for skin, that is used by being in contact with a patient or a tissue taken from a patient such as blood or other body fluids. Particularly, the medical device is useful as, soft ophthalmic lenses, for example, ophthalmic lenses such as a soft ophthalmic lens, for example, a soft contact lens, an intraocular lens, an artificial cornea, a corneal inlay, a corneal onlay, and spectacle lenses.

REFERENCE SIGNS LIST

1 Apparatus
10 Sample Stage
10a Quartz Glass Plate
11 Measuring Jig (made of aluminum)
12 Friction Detection Part
13 Force Measuring Device
20 Friction Element
21 Mounting Holder (made of aluminum)
22 Gasket (made of "Teflon (registered trademark)")
23 Nut (made of aluminum)
S Sample

The invention claimed is:

1. A medical device comprising:
one or more layers comprising an acidic polymer and one or more layers comprising a basic polymer formed on at least a part of a surface of a base material, wherein
at least one of an acidic polymer and a basic polymer forming the one or more layers is a multi-component copolymer of three or more components.

2. The medical device according to claim 1, wherein the one or more layers are formed by carrying out treatment with one or more acidic polymer solutions one or more times and carrying out treatment with one or more basic polymer solutions one or more times.

3. The medical device according to claim 1, wherein the one or more layers are formed by carrying out treatment with an acidic polymer solution one or two times and carrying out treatment with a basic polymer solution one or two times, and consequently carrying out the treatment three times in total.

4. The medical device according to claim 1, wherein at least one of the acidic polymer and the basic polymer forming the one or more layers is a polymer having a group selected from a hydroxy group and an amide group.

5. The medical device according to claim 1, wherein the multi-component copolymer of three or more components comprises one or more of each of an acidic monomer or a basic monomer, a monomer having a hydroxy group, and a monomer having an amide group.

6. The medical device according to claim 5, wherein the acidic monomer comprises at least one of an acidic group selected from a carboxy group, a sulfonic acid group, and a phosphoric acid group in a molecule thereof.

7. The medical device according to claim 5, wherein the basic monomer comprises an amino group.

8. The medical device according to claim 1, wherein the base material is a low water content base material having a water content of 10% by mass or less.

9. The medical device according to claim 1, wherein the base material comprises a polymer of the following component A or a copolymer of the following component A and component B as a main component:
Component A: a polysiloxane compound having a plurality of polymerizable functional groups per molecule and a number average molecular weight of 6000 or more; and
Component B: a polymerizable monomer having a fluoroalkyl group.

10. The medical device according to claim 9, wherein the component A is a polysiloxane compound represented by the following formula (A1):

(A1)

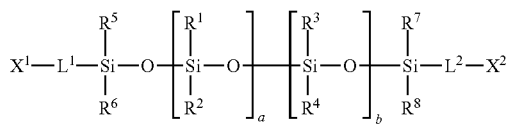

where $X^1$ and $X^2$ each independently represents a polymerizable functional group; $R^1$ to $R^8$ each independently represents a substituent selected from hydrogen, an alkyl group having a carbon number of 1 to 20, a phenyl group, and a fluoroalkyl group having a carbon number of 1 to 20; $L^1$ and $L^2$ each independently represents a divalent group; a and b each independently represents an integer of 0 to 1500; and a and b are not zero at the same time.

11. The medical device according to claim 1, wherein the base material is a hydrogel.

12. The medical device according to claim 11, wherein the base material is a silicone hydrogel containing 5% by mass or more of silicon atoms.

13. The medical device according to claim 1, wherein the medical device is a soft ophthalmic lens.

14. A method for producing a medical device comprising step 1 to step 3 in this order, wherein any one of an acidic polymer and a basic polymer used in the step 2 or 3 is a multi-component copolymer of three or more components, the method comprising:

the step 1 of polymerizing a mixture comprising a monomer having a siloxanyl group to obtain a molding;

the step 2 of contacting the molding to a basic polymer solution, and thereafter, washing and removing the excessive basic polymer solution; and the step 3 of contacting the molding, which has been treated with the basic polymer solution of the step 2, to an acidic polymer solution, and thereafter, washing and removing the excessive acidic polymer solution.

15. A method for producing a medical device comprising step 1 to step 4 in this order, wherein any one of an acidic polymer and a basic polymer used in the steps 2 to 4 is a multi-component copolymer of three or more components, the method comprising:

the step 1 of polymerizing a mixture comprising a monomer having a siloxanyl group to obtain a molding;

the step 2 of contacting the molding to an acidic polymer solution, and thereafter, washing and removing the excessive acidic polymer solution;

the step 3 of contacting the molding, which has been treated with the acidic polymer solution of the step 2, to a basic polymer solution, and thereafter, washing and removing the excessive basic polymer solution; and the step 4 of contacting the molding, which has been treated with the acidic polymer solution of the step 2 and the basic polymer solution of the step 3, to an acidic polymer solution being the same as or different from the acidic polymer in the step 2, and thereafter, washing and removing the excessive acidic polymer solution.

* * * * *